US012780808B2

(12) United States Patent
Grill

(10) Patent No.: US 12,780,808 B2
(45) Date of Patent: Nov. 3, 2026

(54) SAFRYLAMINE DERIVATIVES HAVING PRODRUG PROPERTIES

(71) Applicant: MiHKAL GmbH, Allschwil (CH)

(72) Inventor: Matthias Grill, Basel (CH)

(73) Assignee: MiHKAL GmbH, Allschwil (CH)

( * ) Notice: Subject to any disclaimer, the term of this patent is extended or adjusted under 35 U.S.C. 154(b) by 804 days.

(21) Appl. No.: 18/024,517

(22) PCT Filed: Sep. 13, 2021

(86) PCT No.: PCT/EP2021/075142
§ 371 (c)(1),
(2) Date: Mar. 3, 2023

(87) PCT Pub. No.: WO2022/053696
PCT Pub. Date: Mar. 17, 2022

(65) Prior Publication Data

US 2023/0322743 A1 Oct. 12, 2023

(30) Foreign Application Priority Data

Sep. 11, 2020 (DE) ......................... 102020123793.6

(51) Int. Cl.
*C07D 405/12* (2006.01)
*A61P 25/00* (2006.01)
*C07D 317/58* (2006.01)
*C07D 317/70* (2006.01)

(52) U.S. Cl.
CPC ............ *C07D 405/12* (2013.01); *A61P 25/00* (2018.01); *C07D 317/58* (2013.01); *C07D 317/70* (2013.01)

(58) Field of Classification Search
CPC ................ C07D 405/12; C07D 317/58; C07D 317/70; A61P 25/00
See application file for complete search history.

(56) References Cited

U.S. PATENT DOCUMENTS

2009/0131335 A1 † 5/2009 Mickle

FOREIGN PATENT DOCUMENTS

WO WO-2009095479 A2 * 8/2009 ............ A61K 47/65

OTHER PUBLICATIONS

Collins et al. Drug Test. Analysis. 2017; 9: 399-404 (Year: 2017).*
Saez-Briones et al. (Curr Neuropharmacol. 2013;11(5):521-534). (Year: 2013).*
Leuthi et al (Arch Toxicol. 2020;94(4):1085-1133). (Year: 2020).*
Murnane (Behav Pharmacol. 2019;30(2-):151-162). (Year: 2019).*
Liechti, Matthias E., MDMA Prodrugs to Assist Psychotherapy, 45 pages, Nov. 18, 2020, U.S. Appl. No. 63/115,245 of U.S. Appl. No. 17/518,846.†
Mazur, Robert H., Structure-Taste Relationships of Aspartic Acid Amides, 5 pages, Nov. 1, 1970, Journal of Medicinal Chemistry, vol. 13(6), DOI:10.1021/jm00300a046.†
Gatch, Michael, Locomotor, discriminative stimulus, and place conditioning effects of MDAI in rodents, 18 pages, Sep. 1, 2017, Behavioral Pharmacology, vol. 27(6), DOI: 10.1097/FBP.0000000000000237.†
Nichols, David E., Synthesis and Evaluation of 2,3-Dihydrobenzofuran Analogues of the Hallucinogen 1-(2,5-Dimethoxy-4methylphenyl)-2-aminopropane: Drug Discrimination Studies in Rats, 3 pages, Feb. 1, 1986, Journal of Medicinal Chemistry, vol. 29(2), DOI: 10.1021/jm00152a022.†
Bahji, Anees, Efficacy of 3,4-methylenedioxymethamphetamine (MDMA)-assisted psychotherapy for posttraumatic stress disorder: A systematic review and meta-analysis, 15 pages, Aug. 19, 2019, Progress in Neuropsychopharmacology &Biological Psychiatry, vol. 96, DOI: 10.1016/j.pnpbp.2019.109735.†

* cited by examiner
† cited by third party

*Primary Examiner* — Clinton A Brooks
*Assistant Examiner* — Jerica Katlynn Wilson
(74) *Attorney, Agent, or Firm* — Greenberg Traurig, LLP

(57) ABSTRACT

The present invention provides a novel group of active peptide compounds based on the psychoactive safrylamine compounds MDMA, MDA, MMDA-2, and MDAI. Thereby, the invention provides for improved pharmacokinetic properties during uptake of the safrylamines, as well as reduced side effects resulting from the metabolites thus formed. Due to the affinity of the novel safrylamine derivatives for the 5-HT2a-receptor, the invention can find use in numerous forms of therapy, such as against depression or posttraumatic stress disorder (PTSD).

13 Claims, 14 Drawing Sheets

SAFRYLAMINE DERIVATIVES HAVING PRODRUG PROPERTIES

CROSS-REFERENCE TO RELATED PATENT APPLICATIONS

The present application is a National Stage Entry of International Patent Application No. PCT/EP2021/075142, filed Sep. 13, 2021, titled "NOVEL SAFRYLAMINE DERIVATIVES HAVING PRODRUG PROPERTIES", which claims priority to and benefit of German patent application DE 10 2020 123 793.6 filed on Sep. 11, 2020, the content of each are incorporated herein by reference in its their entirety.

The present invention provides a series of novel active compounds based on the prodrug concept for four psychoactive safrylamines. Thereby, an appropriate selection of the adducts provides for modified pharmacokinetic properties during uptake of the respective empathogens, as well as reduced side effects resulting from the metabolites thus formed. Due to the affinity of the active safrylamine compounds inter alia for the 5-HT2a-receptor, the invention can find use in numerous forms of therapy, such as against depression or posttraumatic stress disorder (PTSD).

BACKGROUND 3,4-Methylenedioxy-N-methylamphetamine (MDMA) was filed for a patent for the first time by Anton Köllisch for the company Merck in 1914. Since then, numerous analogous compounds have been synthesized by scientists like Alexander Shulgin and David Nichols. Among the best known of these analogues are 3,4-methylenedioxyamphetamine (MDA), 2-methoxy-4,5-methylenedioxyamphetamine (MMDA-2), and 5,6-methylenedioxy-2-aminoindane (MDAI).

As MDMA is both an agonist of serotonin receptors and, at the same time, a serotonin re-uptake inhibitor, chronic or even acute symptoms may be observed after repeated administration. The effects of this substance class are not selectively restricted to the serotonin system, but may, to a lesser degree, be detected both in the adrenergic and the dopaminergic system as well. This may result in side effects such as sleeping disorders and even hyperthermia and dehydration. In the past, there were regrettably cases to be documented, in which the mixed abuse of MDMA combined with insufficient fluid intake resulted in a fatal outcome.

Furthermore, MDMA has often been associated with the undesired effect of a "serotonin syndrome". This syndrome is triggered by a too high concentration of serotonin in the neurons, as it was already observed with some other active compounds (e.g., MAO inhibitors or antidepressants). An, at times, too extreme variation in serotonin concentrations within the neurons and the formation of certain neurotoxic metabolites of MDMA appear to be responsible for its neurotoxic properties. This caused medical chemists like Prof. Nichols to further develop the MDMA on a molecular level. In his publications from the 1990s, he presented the presumably non-neurotoxic MDAI.

An accurate explanation of the real mechanism of neuronal damaging by this group of substances could not be given to date. However, it is very likely that too fast an increase in concentration of the active compound within neurons/synapses is worsening these symptoms substantially. From a pharmacological point of view, active compounds would be advantageous which could be released into the CNS more retardedly. The aim, however, is to thereby not only alter the pharmacokinetic component of the active compound but also to prevent a fluctuating synaptic concentration of serotonin.

Even though the extent of neurotoxicity of the basic active compounds (MDMA, MDA, and MDAI) could not be entirely elucidated until today, the active compound MDMA has found use worldwide in psycholytic therapy of anxiety conditions and depression since the 1990s. In particular, the treatment of posttraumatic stress disorder (PTSD) has been advanced by the organization MAPS (Multidisciplinary Association for Psychedelic Studies) for more than 20 years. Meanwhile, clinical phase III studies are being conducted with the aim of receiving approval by the FDA and EMA for the active compound MDMA in the treatment of PTSD.

Novel active compounds similar to MDMA, in particular those showing a modified (accelerated or retarded) activity in the human body due to their structure and consequently having a more favorable side-effect profile, are thus of increasing pharmaceutical interest. Another important property of the thus designed "peptide prodrugs" is a significantly decreased potential for abuse in reality because these compounds do not give rise to expect a rapid "flooding" of the psychoactive phenethylamine in the human organism even at intravenous or intranasal application, and thus trigger dependencies to a lesser extent. Against this backdrop, novel, easily producible safrylamine derivatives based on peptides have been developed and are presented in the present invention.

DETAILED DESCRIPTION

Figure 1:
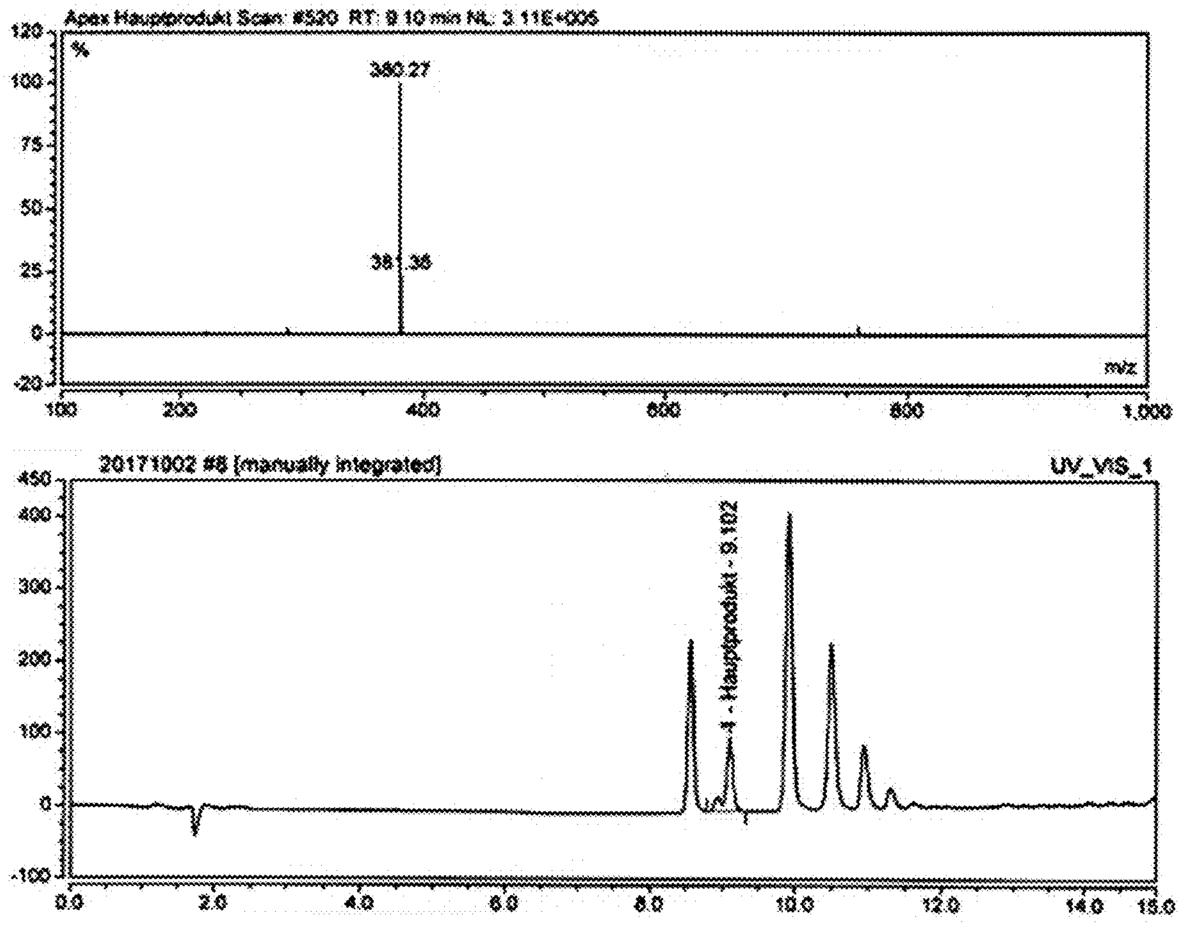
FIG. 1: HPLC-MS spectrum of 3,4-methylenedioxy-N-methylamphetamine-N'-L-tryptophanamide from the reaction solution.
Figure 2:
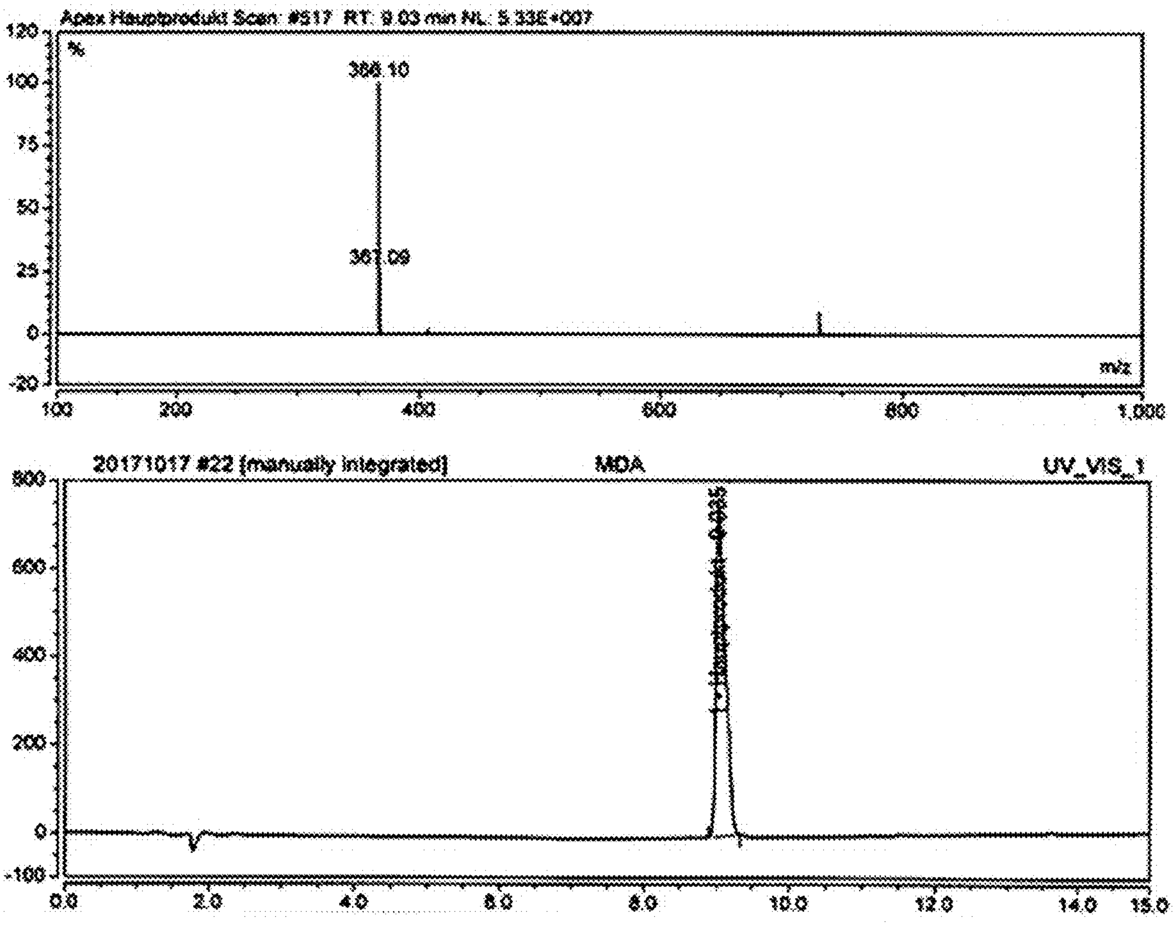
FIG. 2: HPLC-MS spectrum of 3,4-methylenedioxyamphetamine-N-L-tryptophanamide.
Figure 3:
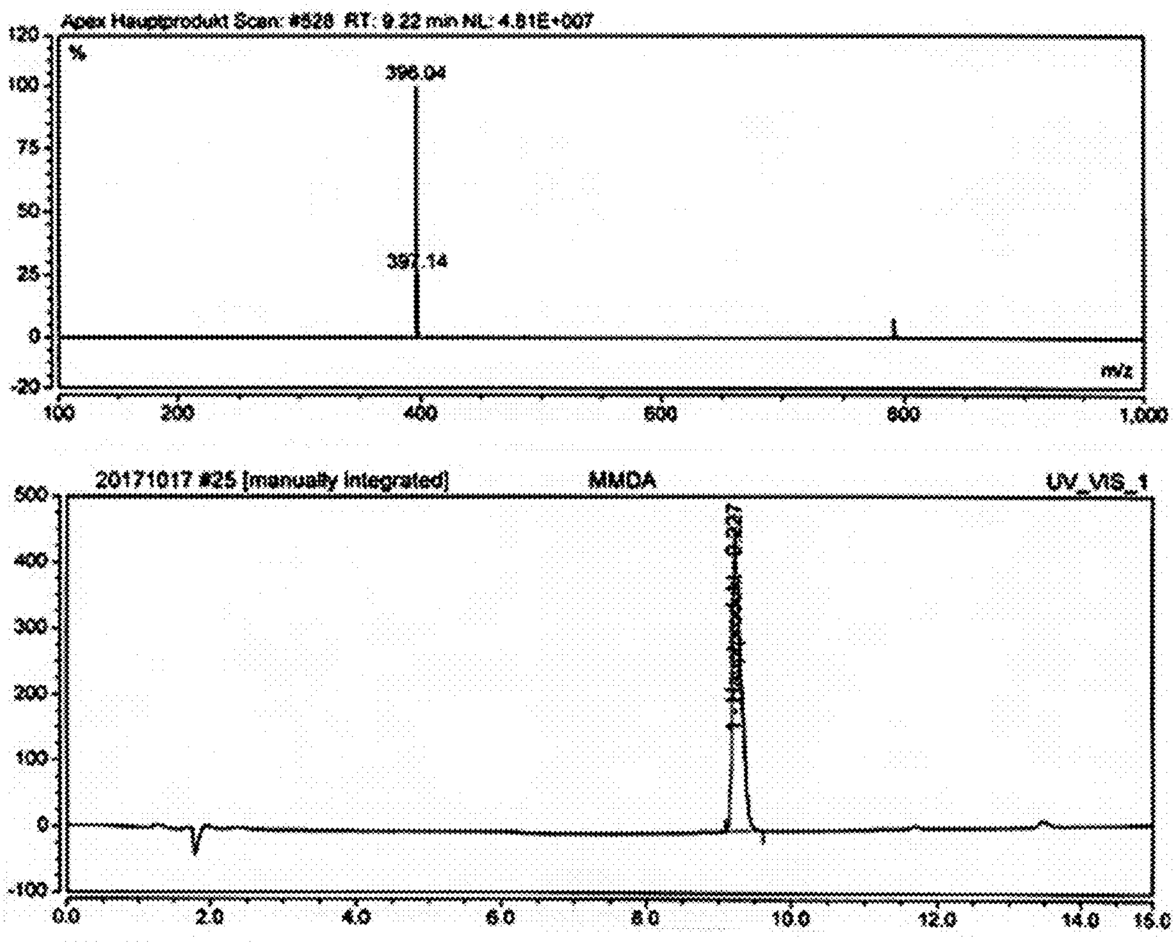
FIG. 3: HPLC-MS spectrum of 2-methoxy-4,5-methylenedioxyamphetamine-N-L-tryptophanamide.
Figure 4:
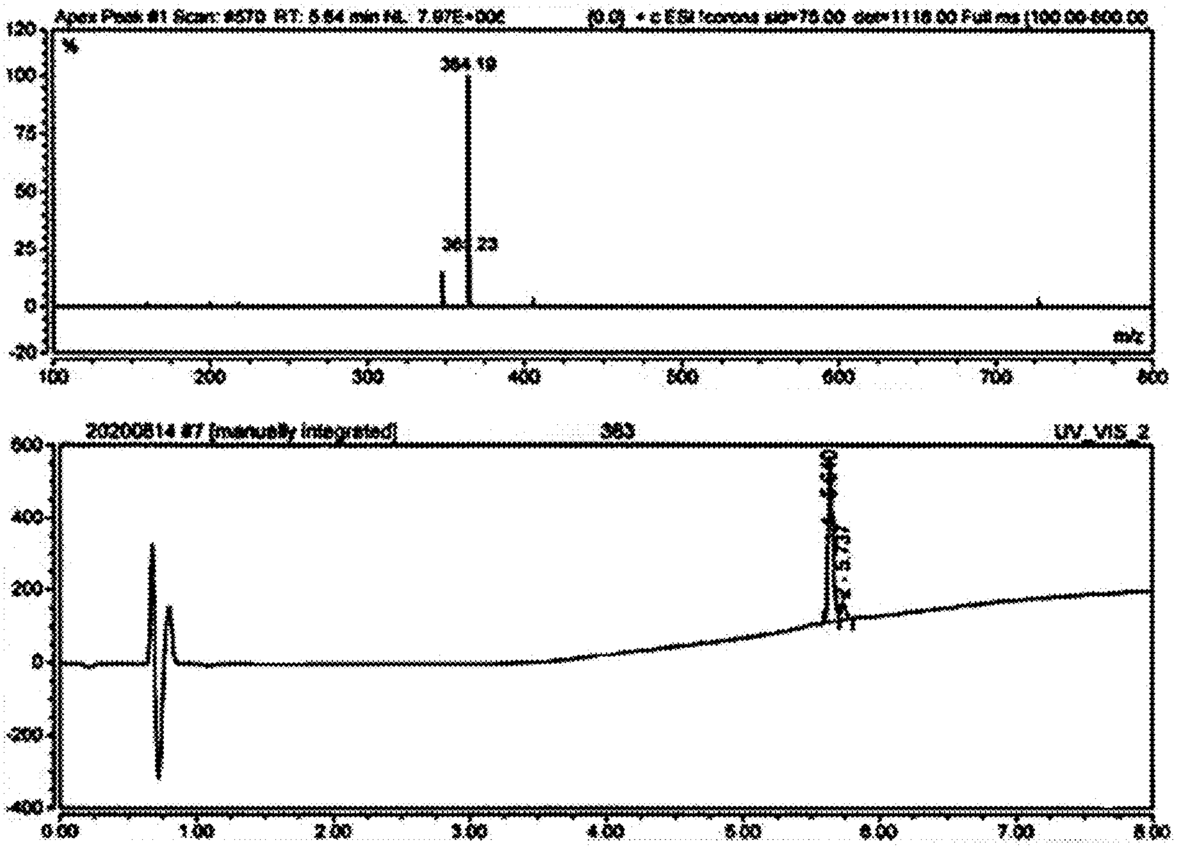
FIG. 4: HPLC-MS spectrum of 5,6-methylenedioxy-2-aminoindane-N-L-tryptophanamide.
Figure 5:
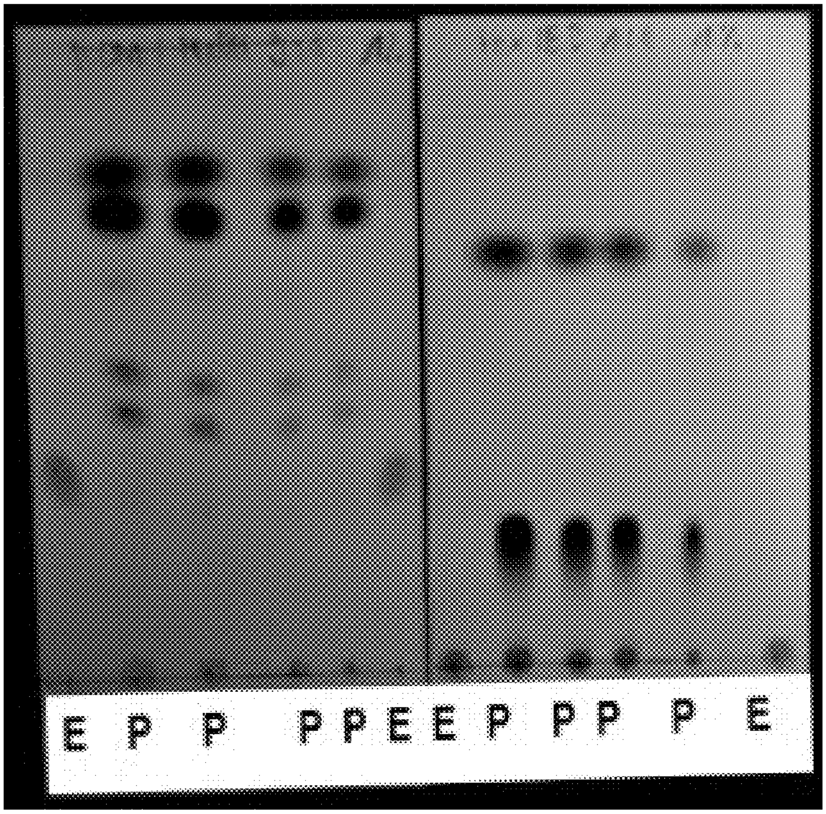
FIG. 5: Thin layer chromatograms of the reactant 3,4-methylenedioxyamphetamine (E) and a sample of the reaction mixture of the Fmoc-protected intermediate product of 3,4-methylenedioxyamphetamine-N-L-tryptophanamide (P) in hexane/ethyl acetate 1:1 and dichloromethane/methanol 9:1, respectively.
Figure 6:
FIG. 6: Thin layer chromatogram of the Fmoc-protected intermediate product of 3,4-methylenedioxyamphetamine-N-L-tryptophanamide (E) and a sample of the reaction mixture of the product according to the invention 3,4-methylenedioxyamphetamine-N-L-tryptophanamide during the deprotection in hexane/ethyl acetate 1:1 after 1 hour (1 h) and 48 hours (48 h).
Figure 7:
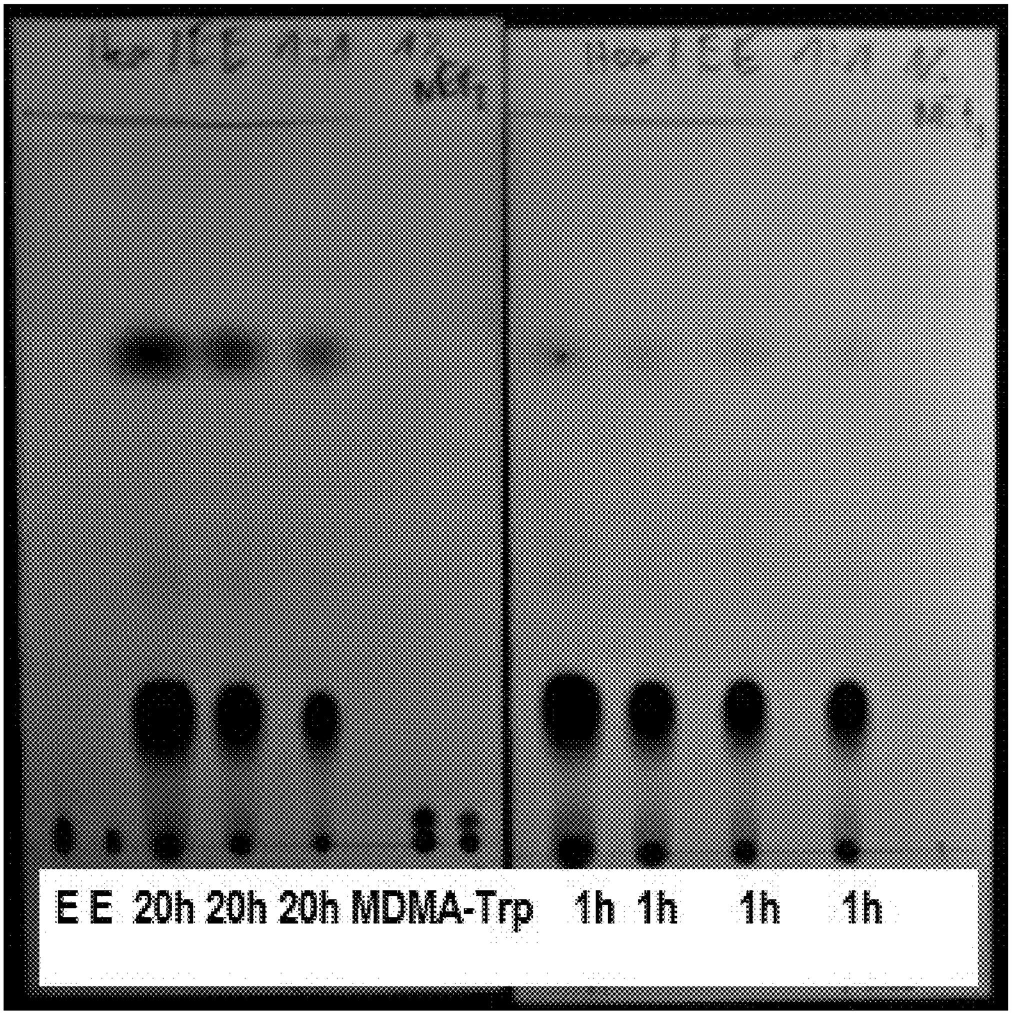
FIG. 7: Thin layer chromatograms of the reactant 2-methoxy-4,5-methylenedioxyamphetamine (E) and a sample of the reaction mixture of the Fmoc-protected intermediate product of 2-methoxy-4,5-methylenedioxyamphetamine-N-L-tryptophanamide after 1 hour and 20 hours (1 h/20 h) and the product according to the invention 3,4-methylenedioxy-N-methylamphetamine-N'-L-tryptophanamide (MDMA-Trp) in hexane/ethyl acetate 1:1.
Figure 8:
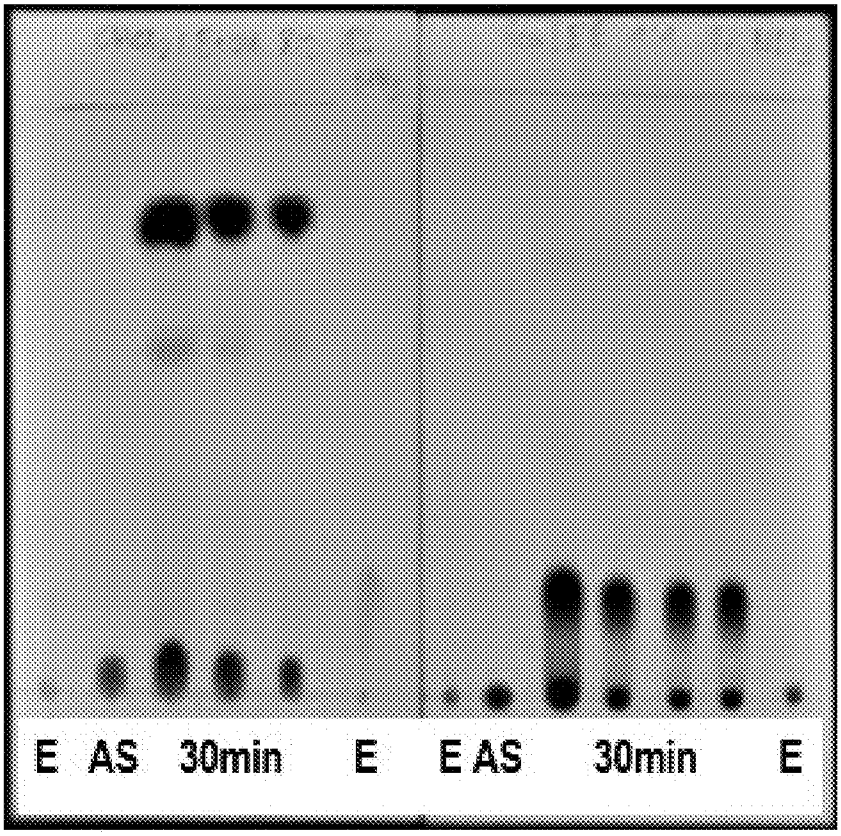
FIG. 8: Thin layer chromatograms of the reactant 5,6-methylenedioxy-2-aminoindane (E), the Fmoc-protected tryptophan (AS) and a sample of the reaction mixture of the Fmoc-protected intermediate product of 5,6-methylenedioxy-2-aminoindane-N-L-tryptophanamide (30 min) in hexane/ethyl acetate 1:1 and chloroform/ethanol 8:2, respectively.

Definitions:

For convenience, certain terms employed in the specification, examples and claims are collected here. Unless defined otherwise, all technical and scientific terms used in this disclosure have the same meanings as commonly understood by one of ordinary skill in the art to which this disclosure belongs.

As used herein, unless explicitly indicated otherwise or contradicted by context, the terms "a", "an" and "the" are used interchangeably with "one or more" and "at least one". Thus, for example, a composition comprising "a" compound of formula (I) can be interpreted as referring to a composition comprising "one or more" compounds of formula (I).

The terms "administer," "administering" or "administration" as used herein refer to administering a compound or pharmaceutically acceptable salt of the compound or a composition or formulation comprising the compound or pharmaceutically acceptable salt of the compound to a patient.

As used herein, the term "comprising" (or "comprise", "comprises", etc.), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

The terms "effective amount" and "therapeutically effective amount" are used herein interchangeably and refer to an amount of a compound or a salt thereof (or a pharmaceutical composition containing the compound or salt) that, when administered to a subject/patient, is capable of performing the intended result. The "effective amount" will vary depending on the active ingredient, the state, disorder or condition to be treated and its severity, and the age, weight, physical condition and responsiveness of the subject/patient to be treated.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, if a component of a composition is indicated to be "optional", the invention specifically relates to both possibilities, i.e., that the corresponding component is present (contained in the composition) or that the corresponding component is absent from the composition.

As used herein, the term "treatment" (or "treating") in relation to a disease or disorder refers to the management and care of a patient for the purpose of combating the disease or disorder, such as to reverse, alleviate, inhibit or delay the disease or disorder, or one or more symptoms of such disease or disorder. It also refers to the administration of a compound or a composition for the purpose of preventing the onset of symptoms of the disease or disorder, alleviating such symptoms, or eliminating the disease or disorder. Preferably, the "treatment" is curative, ameliorating or palliative.

As used herein, the term "hydrocarbon group" refers to a group consisting of carbon atoms and hydrogen atoms.

As used herein, the term "alicyclic" is used in connection with cyclic groups and denotes that the corresponding cyclic group is non-aromatic.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Exemplary alkyl groups include methyl, ethyl, propyl (e.g., n-propyl or isopropyl), or butyl (e.g., n-butyl, isobutyl, sec-butyl, or tert-butyl).

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Exemplary alkenyl groups include ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl).

As used herein, the term "alkynyl" refers to a monovalent unsaturated acyclic hydrocarbon group which may be linear or branched and comprises one or more (e.g., one or two) carbon-to-carbon triple bonds and optionally one or more (e.g., one or two) carbon-to-carbon double bonds. The term "$C_{2-5}$ alkynyl" denotes an alkynyl group having 2 to 5 carbon atoms. Exemplary alkynyl groups include ethynyl, propynyl (e.g., propargyl), or butynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present. Exemplary alkylene groups include methylene ($—CH_2—$), ethylene (e.g., $—CH_2—CH_2—$ or $—CH(—CH_3)—$), propylene (e.g., $—CH_2—CH_2—CH_2—$, $—CH(—CH_2—CH_3)—$, $—CH_2—CH(—CH_3)—$, or $—CH(—CH_3)—CH_2—$), or butylene (e.g., $—CH_2—CH_2—CH_2—CH_2—$).

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. "Carbocyclyl" may, e.g., refer to aryl, cycloalkyl or cycloalkenyl.

As used herein, the term "carbocyclylene" refers to a carbocyclyl group, as defined herein above, but having two points of attachment, i.e. a divalent hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. "Carbocyclylene" may, e.g., refer to arylene, cycloalkylene or cycloalkenylene.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocyclyl" may, e.g., refer to heteroaryl, heterocycloalkyl or heterocycloalkenyl.

As used herein, the term "heterocyclylene" refers to a heterocyclyl group, as defined herein above, but having two points of attachment, i.e. a divalent ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocyclylene" may, e.g., refer to heteroarylene, heterocycloalkylene or heterocycloalkenylene.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). If the aryl is a bridged and/or fused ring system which contains, besides one or more aromatic rings, at least one non-aromatic ring (e.g., a saturated ring or an unsaturated alicyclic ring), then one or more carbon ring atoms in each non-aromatic ring may optionally be oxidized (i.e., to form an oxo group). "Aryl" may, e.g., refer to phenyl, naphthyl, dialinyl (i.e., 1,2-dihydronaphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. In particular, an "aryl" may have 6 to 14 ring atoms, e.g., 6 to 10 ring atoms.

As used herein, the term "arylene" refers to an aryl group, as defined herein above, but having two points of attachment, i.e. a divalent aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). If the arylene is a bridged and/or fused ring system which contains, besides one or more aromatic rings, at least one non-aromatic ring (e.g., a saturated ring or an unsaturated alicyclic ring), then one or more carbon ring atoms in each non-aromatic ring may optionally be oxidized (i.e., to form an oxo group). "Arylene" may, e.g., refer to phenylene (e.g., phen-1,2-diyl, phen-1,3-diyl, or phen-1,4-diyl), naphthylene (e.g., naphthalen-1,2-diyl, naphthalen-1,3-diyl, naphthalen-1,4-diyl, naphthalen-1,5-diyl, naphthalen-1,6-diyl, naphthalen-1,7-diyl, naphthalen-2,3-diyl, naphthalen-2,5-diyl, naphthalen-2,6-diyl, naphthalen-2,7-diyl, or naphthalen-2,8-diyl), 1,2-dihydronaphthylene, 1,2,3,4-tetrahydronaphthylene, indanylene, indenylene, anthracenylene, phenanthrenylene, 9H-fluorenylene, or azulenylene. In particular, an "arylene" may have 6 to 14 ring atoms, e.g., 6 to 10 ring atoms.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 1H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7]phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b]thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazopyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. In particular, the term "heteroaryl" may refer to a 5 to 14 membered (e.g., 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "heteroarylene" refers to a heteroaryl group, as defined herein above, but having two points of attachment, i.e. a divalent aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three, or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroarylene" may, e.g., refer to thienylene (i.e., thiophenylene; e.g., thien-2,3-diyl, thien-2,4-diyl, or thien-2,5-diyl), benzo[b]thienylene, naphtho[2,3-b]thienylene, thianthrenylene, furylene (i.e., furanylene; e.g., furan-2,3-diyl, furan-2,4-diyl, or furan-2,5-diyl), benzofuranylene, isobenzofuranylene, chromanylene, chromenylene, isochromenylene, chromonylene, xanthenylene, phenoxathiinylene, pyrrolylene, imidazolylene, pyrazolylene, pyridylene (i.e., pyridinylene), pyrazinylene, pyrimidinylene, pyridazinylene, indolylene, isoindolylene, indazolylene, indolizinylene, purinylene, quinolylene, isoquinolylene, phthalazinylene, naphthyridinylene, quinoxalinylene, cinnolinylene, pteridinylene, carbazolylene, 3-carbolinylene, phenanthridinylene, acridinylene, perimidinylene, phenanthrolinylene, phenazinylene, thiazolylene (e.g., thiazol-2,4-diyl, thiazol-2,5-diyl, or thiazol-4,5-diyl), isothiazolylene (e.g., isothiazol-3,4-diyl, isothiazol-3,5-diyl, or isothiazol-4,5-diyl), phenothiazinylene, oxazolylene (e.g., oxazol-2,4-diyl, oxazol-2,5-diyl, or oxazol-4,5-diyl), isoxazolylene (e.g., isoxazol-3,4-diyl, isoxazol-3,5-diyl, or isoxazol-4,5-diyl), oxadiazolylene (e.g., 1,2,4-oxadiazol-3,5-diyl, 1,2,5-oxadiazol-3,4-diyl, or 1,3,4-oxadiazol-2,5-diyl), thiadiazolylene (e.g., 1,2,4-thiadiazol-3,5-diyl, 1,2,5-thiadiazol-3,4-diyl, or 1,3,4-thiadiazol-2,5-diyl), phenoxazinylene, pyrazolo[1,5-a]pyrimidinylene, 1,2-benzoisoxazolylene, benzothiazolylene, benzothiadiazolylene, benzoxazolylene, benzisoxazolylene, benzimidazolylene, benzo[b]thiophenylene (i.e., benzothienylene), triazolylene (e.g., 1H-1,2,3-triazolylene, 2H-1,2,3-triazolylene, 1H-1,2,4-triazolylene, or 4H-1,2,4-triazolylene), benzotriazolylene, 1H-tetrazolylene, 2H-tetrazolylene, triazinylene (e.g., 1,2,3-triazinylene, 1,2,4-triazinylene, or 1,3,5-triazinylene), furo[2,3-c]pyridinylene, dihydrofuropyridinylene (e.g., 2,3-dihydrofuro[2,3-c]pyridinylene or 1,3-dihydrofuro[3,4-c]pyridinylene), imidazopyridinylene (e.g., imidazo[1,2-a]pyridinylene or imidazo[3,2-a]pyridinylene), quinazolinylene, thienopyridinylene, tetrahydrothienopyridinylene (e.g., 4,5,6,7-tetrahydrothieno[3,2-c]pyridinylene), dibenzofuranylene, 1,3-benzodioxolylene, benzodioxanylene (e.g., 1,3-benzodioxanylene or 1,4-benzodioxanylene), or coumarinylene. In particular, the term "heteroarylene" may refer to a divalent 5 to 14 membered (e.g., 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. In particular, "cycloalkyl" may refer to a $C_{3-11}$ cycloalkyl, e.g., a $C_{3-7}$ cycloalkyl.

As used herein, the term "cycloalkylene" refers to a cycloalkyl group, as defined herein above, but having two points of attachment, i.e. a divalent saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkylene" may, e.g., refer to cyclopropylene (e.g., cyclopropan-1,1-diyl or cyclopropan-1,2-diyl), cyclobutylene (e.g., cyclobutan-1,1-diyl, cyclobutan-1,2-diyl, or cyclobutan-1,3-diyl), cyclopentylene (e.g., cyclopentan-1,1-diyl, cyclopentan-1,2-diyl, or cyclopentan-1,3-diyl), cyclohexylene (e.g., cyclohexan-1,1-diyl, cyclohexan-1,2-diyl, cyclohexan-1,3-diyl, or cyclohexan-1,4-diyl), cycloheptylene, decalinylene (i.e., decahydronaphthylene), or adamantylene. In particular, "cycloalkylene" may refer to a $C_{3-11}$ cycloalkylene, e.g., a $C_{3-7}$ cycloalkylene.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thiomorpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. In particular, "heterocycloalkyl" may refer to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "heterocycloalkylene" refers to a heterocycloalkyl group, as defined herein above, but having two points of attachment, i.e. a divalent saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkylene" may, e.g., refer to aziridinylene, azetidinylene, pyrrolidinylene, imidazolidinylene, pyrazolidinylene, piperidinylene, piperazinylene, azepanylene, diazepanylene (e.g., 1,4-diazepanylene), oxazolidinylene, isoxazolidinylene, thiazolidinylene, isothiazolidinylene, morpholinylene, thiomorpholinylene, oxazepanylene, oxiranylene, oxetanylene, tetrahydrofuranylene, 1,3-dioxolanylene, tetrahydropyranylene, 1,4-dioxanylene, oxepanylene, thiiranylene, thietanylene, tetrahydrothiophenylene (i.e., thiolanylene), 1,3-dithiolanylene, thianylene, thiepanylene, decahydroquinolinylene, decahydroisoquinolinylene, or 2-oxa-5-aza-bicyclo[2.2.1]hept-5-ylene. In particular, "heterocycloalkylene" may refer to a divalent 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkenyl" refers to an unsaturated alicyclic (non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. In particular, "cycloalkenyl" may refer to a $C_{3-11}$ cycloalkenyl, e.g., a $C_{3-7}$ cycloalkenyl.

As used herein, the term "cycloalkenylene" refers to a cycloalkenyl group, as defined herein above, but having two points of attachment, i.e. a divalent unsaturated alicyclic (i.e., non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenylene" may, e.g., refer to cyclopropenylene, cyclobutenylene, cyclopentenylene, cyclohexenylene, cyclohexadienylene, cycloheptenylene, or cycloheptadienylene. In particular, "cycloalkenylene" may refer to a $C_{3-11}$ cycloalkenylene, e.g., a $C_{3-7}$ cycloalkenylene.

As used herein, the term "heterocycloalkenyl" refers to an unsaturated alicyclic (non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). In particular, "heterocycloalkenyl" may refer to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "heterocycloalkenylene" refers to a heterocycloalkenyl group, as defined herein above, but having two points of attachment, i.e. a divalent unsaturated alicyclic (i.e., non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenylene" may, e.g., refer to imidazolinylene, tetrahydropyridinylene, dihydropyridinylene, pyranylene, thiopyranylene, dihydropyranylene, dihydrofuranylene, dihydropyrazolylene, dihydropyrazinylene, dihydroisoindolylene, octahydroquinolinylene, or octahydroisoquinolinylene. In particular, "heterocycloalkenylene" may refer to a divalent 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (e.g., 1 to 6, or 1 to 3) halogen atoms which are selected independently from fluoro, chloro, bromo and iodo (and which may all be fluoro atoms). It will be understood that the maximum number of halogen atoms is limited by the number of available attachment sites and, thus, depends on the number of carbon atoms comprised in the alkyl moiety of the haloalkyl group. "Haloalkyl" may, e.g., refer to $—CF_3$, $—CHF_2$, $—CH_2F$, $—CF_2—CH_3$, $—CH_2—CF_3$, $—CH_2—CF_3$, $—CH_2—CHF_2$, $—CH_2—CF_2—CH_3$, $—CH_2—CF_2—CF_3$, or $—CH(CF_3)_2$.

The terms "bond" and "covalent bond" are used herein synonymously, unless explicitly indicated otherwise or contradicted by context.

Various groups are referred to herein as being "optionally substituted". Generally, these groups may carry one or more substituents, such as, e.g., one, two, three or four substituents. It will be understood that the maximum number of substituents is limited by the number of attachment sites available on the substituted moiety. Alternatively, the optional substituents may be absent, i.e., the corresponding groups may be unsubstituted.

It is to be understood that wherever numerical ranges are provided/disclosed herein, all values and subranges encompassed by the respective numerical range are meant to be encompassed within the scope of the invention. Accordingly, the present invention specifically and individually relates to each value that falls within a numerical range disclosed herein, as well as each subrange encompassed by a numerical range disclosed herein.

It is further to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

Compounds of the Present Disclosure:

The present invention addresses the shortcomings in the state of the art, as discussed in the background section above, and provides novel and easily producible peptide-based safrylamine prodrugs ("safrylamine peptides") that have been found to exhibit advantageous pharmacokinetic properties and a beneficial side effect profile, which renders the compounds provided herein particularly well suitable for therapeutic use.

In particular, as a result of the specific design of the active compounds of this invention, particularly by using the derivatization variant of the "tryptophan peptide", the above-described undesirable symptoms could be counteracted in a twofold manner, since following the uptake of the “tryptophan peptide” into the organism, tryptophan gets simultaneously released by the body’s own enzymes and may then be converted into endogenous serotonin which thus supports the “stabilization” of the endogenous serotonin balance.

In one aspect, the present invention provides novel derivatives of 3,4-methylenedioxyamphetamine (“MDA” or safrylamine) according to the following formula (I) as well as pharmaceutically acceptable salts thereof:

(I)

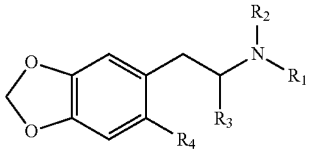

In formula (I), the group $R_1$ is:

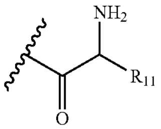 or 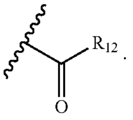

$R_{11}$ is selected from the group consisting of hydrogen, $C_{1-20}$ alkyl, $C_{1-20}$ alkenyl, and $C_{2-20}$ alkynyl, wherein said alkyl, said alkenyl and said alkynyl are each optionally substituted with one or more (e.g., one, two, three, four, or five) groups $R_{13}$, and further wherein one or more (e.g., one, two, three, or four) —$CH_2$— units comprised in said alkyl, said alkenyl or said alkynyl are each optionally replaced by a group $R_{14}$.

$R_{12}$ is a heterocyclyl, wherein said heterocyclyl is attached via a ring carbon atom that is directly adjacent to a ring nitrogen atom, and further wherein said heterocyclyl is optionally substituted with one or more (e.g., one, two, three, four, or five) groups $R_{15}$. In particular, $R_{12}$ may be a heterocyclyl, which is attached via a ring carbon atom that is directly adjacent to a ring nitrogen atom, wherein said heterocyclyl is optionally substituted with one or more $R_{15}$, and wherein said heterocyclyl is a heterocycloalkyl, a heterocycloalkenyl, or a heteroaryl (wherein said heterocycloalkyl, said heterocycloalkenyl, or said heteroaryl may each be monocyclic or polycyclic, e.g., bicyclic or tricyclic).

Each $R_{13}$ is independently selected from the group consisting of —$OR_{16}$, —$NR_{16}R_{16}$, —$COR_{16}$, —$COOR_{16}$, —$OCOR_{16}$, —$CONR_{16}R_{16}$, —$NR_{16}COR_{16}$, —$NR_{16}COOR_{16}$, —$OCONR_{16}R_{16}$, —$SR_{16}$, —$SOR_{16}$, —$SO_2R_{16}$, —$SO_2NR_{16}R_{16}$, —$NR_{16}SO_2R_{16}$, —$SO_3R_{16}$, halogen, $C_{1-10}$ haloalkyl, —O($C_{1-10}$ haloalkyl), —CN, —$NO_2$, carbocyclyl, and heterocyclyl, wherein said carbocyclyl and said heterocyclyl are each optionally substituted with one or more (e.g., one, two or three) groups $R_{15}$.

Each $R_{14}$ is independently selected from the group consisting of —O—, —$NR_{16}$—, —CO—, —S—, —SO—, —$SO_2$—, carbocyclylene, and heterocyclylene, wherein said carbocyclylene and said heterocyclylene are each optionally substituted with one or more (e.g., one, two or three) groups $R_{15}$.

Each $R_{15}$ is independently selected from the group consisting of $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —($C_{1-3}$ alkylene)-OH, —($C_{1-3}$ alkylene)-O($C_{1-5}$ alkyl), —SH, —S($C_{1-5}$ alkyl), —S($C_{1-5}$ alkylene)-SH, —S($C_{1-5}$ alkylene)-S($C_{1-5}$ alkyl), —$NH_2$, —NH($C_{1-5}$ alkyl), —N($C_{1-5}$ alkyl)($C_{1-5}$ alkyl), —NH—OH, —N($C_{1-5}$ alkyl)-OH, —NH—O($C_{1-5}$ alkyl), —N($C_{1-5}$ alkyl)-O($C_{1-5}$ alkyl), halogen, $C_{1-5}$ haloalkyl, —O—($C_{1-5}$ haloalkyl), —CN, —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), —SO—($C_{1-5}$ alkyl), —($C_{0-3}$ alkylene)-carbocyclyl, and —($C_{0-3}$ alkylene)-heterocyclyl, wherein the carbocyclyl group in said —($C_{0-3}$ alkylene)-carbocyclyl and the heterocyclyl group in said —($C_{0-3}$ alkylene)-heterocyclyl are each optionally substituted with one or more groups independently selected from the group consisting of $C_{1-5}$ alkyl, $C_{2-5}$ alkenyl, $C_{2-5}$ alkynyl, halogen, $C_{1-5}$ haloalkyl, —O—($C_{1-5}$ haloalkyl), —CN, —OH, —O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), —CHO, —CO($C_{1-5}$ alkyl), —COOH, —COO($C_{1-5}$ alkyl), —O—CO($C_{1-5}$ alkyl), —CO—$NH_2$, —CO—NH($C_{1-5}$ alkyl), —CO—N($C_{1-5}$ alkyl)($C_{1-5}$ alkyl), —NH—CO($C_{1-5}$ alkyl), —N($C_{1-5}$ alkyl)-CO($C_{1-5}$ alkyl), —NH—COO($C_{1-5}$ alkyl), —N($C_{1-5}$ alkyl)-COO($C_{1-5}$ alkyl), —O—CO—NH($C_{1-5}$ alkyl), —O—CO—N($C_{1-5}$ alkyl)($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —$SO_2$—($C_{1-5}$ alkyl), and —SO—($C_{1-5}$ alkyl).

Each $R_{16}$ is independently selected from the group consisting of hydrogen, $C_{1-5}$ alkyl, $C_{2-5}$ alkenyl, $C_{2-5}$ alkynyl, —($C_{1-5}$ alkylene)-OH, —($C_{1-5}$ alkylene)-O($C_{1-5}$ alkyl), —($C_{1-5}$ alkylene)-O($C_{1-5}$ alkylene)-OH, —($C_{1-5}$ alkylene)-O($C_{1-5}$ alkylene)-O($C_{1-5}$ alkyl), —($C_{1-5}$ alkylene)-SH, —($C_{1-5}$ alkylene)-S($C_{1-5}$ alkyl), —($C_{1-5}$ alkylene)-S($C_{1-5}$ alkylene)-SH, —($C_{1-5}$ alkylene)-S($C_{1-5}$ alkylene)-S($C_{1-5}$ alkyl), —($C_{1-5}$ alkylene)-$NH_2$, —($C_{1-5}$ alkylene)-NH($C_{1-5}$ alkyl), —($C_{1-5}$ alkylene)-N($C_{1-5}$ alkyl)($C_{1-5}$ alkyl), —($C_{1-5}$ alkylene)-NH—OH, —($C_{1-5}$ alkylene)-N($C_{1-5}$ alkyl)-OH, —($C_{1-5}$ alkylene)-NH—O($C_{1-5}$ alkyl), —($C_{1-5}$ alkylene)-N($C_{1-5}$ alkyl)-O($C_{1-5}$ alkyl), —($C_{1-5}$ alkylene)-halogen, —($C_{1-5}$ alkylene)-($C_{1-5}$ haloalkyl), —($C_{1-5}$ alkylene)-O—($C_{1-5}$ haloalkyl), —($C_{1-5}$ alkylene)-$CF_3$, —($C_{1-5}$ alkylene)-CN, —($C_{1-5}$ alkylene)-$NO_2$, —($C_{1-5}$ alkylene)-CHO, —($C_{1-5}$ alkylene)-CO—($C_{1-5}$ alkyl), —($C_{1-5}$ alkylene)-COOH, —($C_{1-5}$ alkylene)-CO—O—($C_{1-5}$ alkyl), —($C_{1-5}$ alkylene)-O—CO—($C_{1-5}$ alkyl), —($C_{1-5}$ alkylene)-CO—$NH_2$, —($C_{1-5}$ alkylene)-CO—NH($C_{1-5}$ alkyl), —($C_{1-5}$ alkylene)-CO—N($C_{1-5}$ alkyl)($C_{1-5}$ alkyl), —($C_{1-5}$ alkylene)-NH—CO—($C_{1-5}$ alkyl), —($C_{1-5}$ alkylene)-N($C_{1-5}$ alkyl)-CO—($C_{1-5}$ alkyl), —($C_{1-5}$ alkylene)-NH—CO—O—($C_{1-5}$ alkyl), —($C_{1-5}$ alkylene)-N($C_{1-5}$ alkyl)-CO—O—($C_{1-5}$ alkyl), —($C_{1-5}$ alkylene)-O—CO—NH—($C_{1-5}$ alkyl), —($C_{1-5}$ alkylene)-O—CO—N($C_{1-5}$ alkyl)-($C_{1-5}$ alkyl), —($C_{1-5}$ alkylene)-$SO_2$—$NH_2$, —($C_{1-5}$ alkylene)-$SO_2$—NH($C_{1-5}$ alkyl), —($C_{1-5}$ alkylene)-$SO_2$—N($C_{1-5}$ alkyl)($C_{1-5}$ alkyl), —($C_{1-5}$ alkylene)-NH—$SO_2$—($C_{1-5}$ alkyl), —($C_{1-5}$ alkylene)-N($C_{1-5}$ alkyl)-$SO_2$—($C_{1-5}$ alkyl), —($C_{1-5}$ alkylene)-$SO_2$—($C_{1-5}$ alkyl), —($C_{1-5}$ alkylene)-SO—($C_{1-5}$ alkyl), —($C_{0-5}$ alkylene)-carbocyclyl, and —($C_{0-5}$ alkylene)-heterocyclyl, wherein the carbocyclyl in said —($C_{0-5}$ alkylene)-carbocyclyl and the heterocyclyl in said —($C_{0-5}$ alkylene)-heterocyclyl are each optionally substituted with one or more (e.g., one, two or three) groups $R_{15}$.

$R_2$ is —H (i.e., hydrogen) or —$CH_3$ (i.e., methyl).

$R_3$ is —$CH_3$, and $R_4$ is —H or —$OCH_3$ (i.e., methoxy), or alternatively $R_3$ and $R_4$ are mutually joined to form a group —$CH_2$— (i.e., methylene).

In certain embodiments, $R_1$ is an α-amino acid which is attached via a CO group formed from a carboxylic acid group comprised in said α-amino acid, wherein said α-amino acid is selected from glycine, alanine, valine, isoleucine, leucine, neopentylglycine, asparagine, glutamine, aspartic acid, glutamic acid, lysine, serine, threonine, tyrosine, tryptophan, proline, pyroglutamic acid, pipecolic acid, ornithine, citrulline, DOPA, diaminopimelic acid, pyrrolysine, norvaline, norleucine, isovaline, homoserine, isoserine, serine-O-methyl ester, threonine-O-methyl ester, lanthionine, 4-hydroxyproline, 4-methylproline, 4-fluoroproline, and any one of the aforementioned groups which is substituted with one or more (e.g., one, two or three) halogen atoms (e.g., fluoro atoms).

Preferably, $R_1$ is selected from the group consisting of:

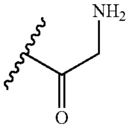 , 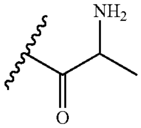 , 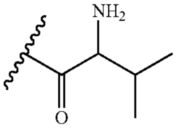 ,

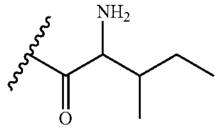 , 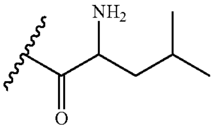 ,

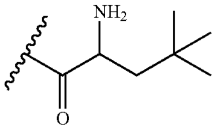 , 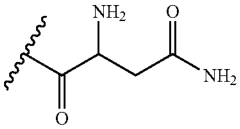 ,

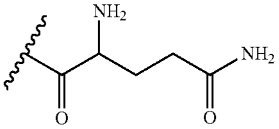 , 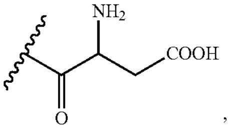 ,

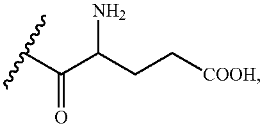

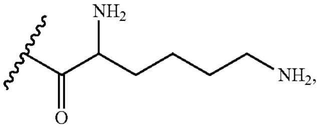

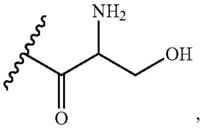 , 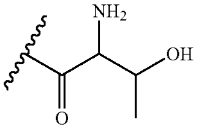 ,

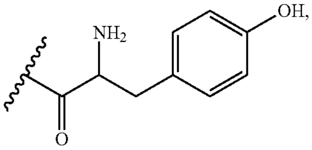

-continued

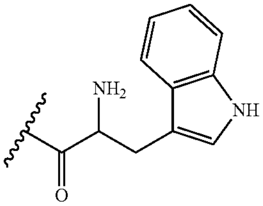 , 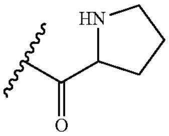 ,

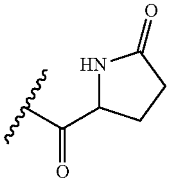 , and 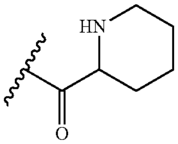 .

In relation to the compounds of formula (I) and the pharmaceutically acceptable salts thereof, the following proviso applies: if $R_2$ is —H, $R_3$ is —$CH_3$ and $R_4$ is —H, then $R_1$ is not

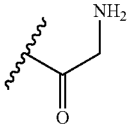 , 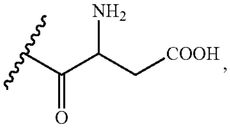 , or

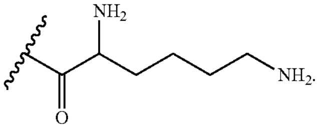

In some embodiments, the present disclosure provides a compound of formula (I) or a pharmaceutically acceptable salt thereof, wherein: $R_2$ is —H; $R_3$ is —$CH_3$; $R_4$ is —H; and $R_1$ is selected from the group consisting of:

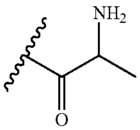 , 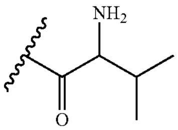 ,

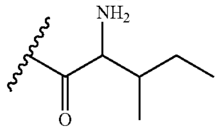 , 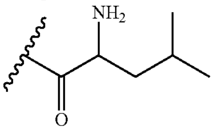 ,

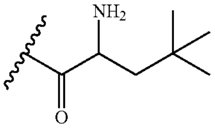 , 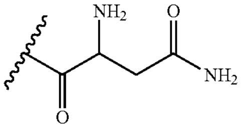 ,

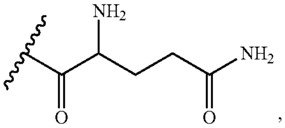 ,

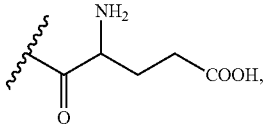

-continued

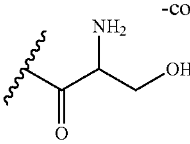
,
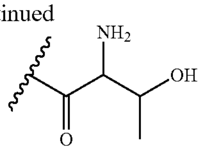
,

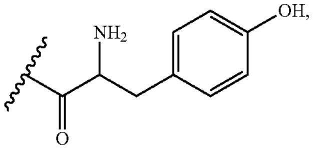

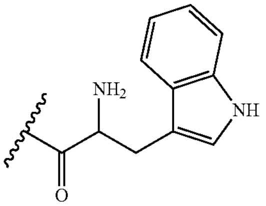
,
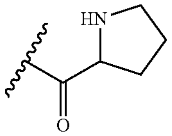
,

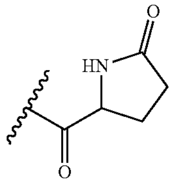
, and
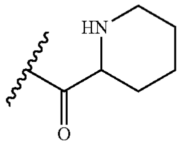
.

In some embodiments, the compound of formula (I) is a compound having the following formula (II):

(II)

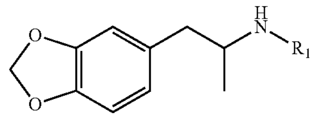

or a pharmaceutically acceptable salt thereof; wherein $R_1$ is selected from the group consisting of:

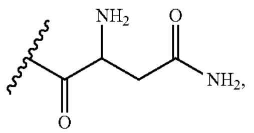

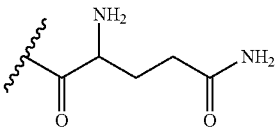
,
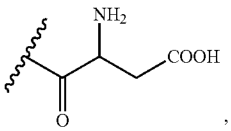
,

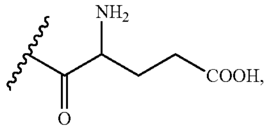

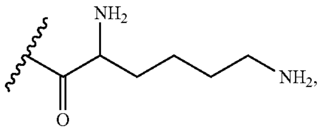

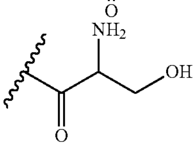
,
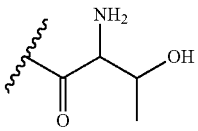
,

-continued

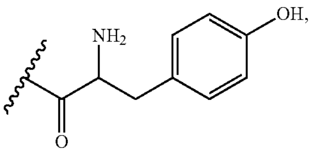

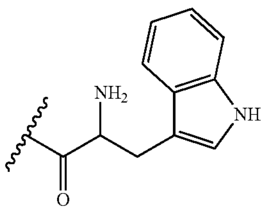
,
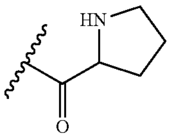
,

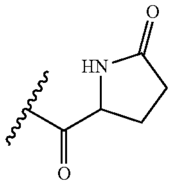
, and
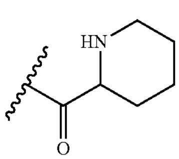
.

In some embodiments, the present disclosure provides a compound of formula (I) or a pharmaceutically acceptable salt thereof, wherein: $R_2$ is —$CH_3$—; $R_3$ is —$CH_3$—; $R_4$ is —H; and $R_1$ is selected from the group consisting of:

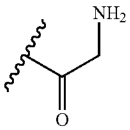
,
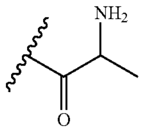
,
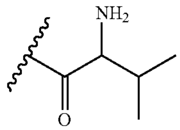
,

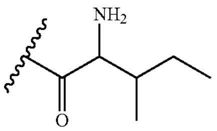
,
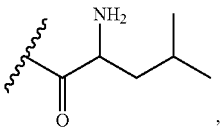
,

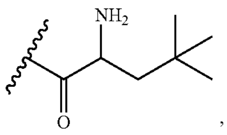
,
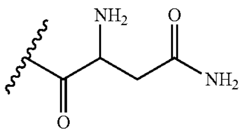
,

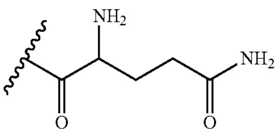
,
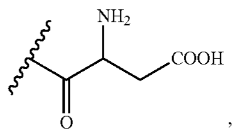
,

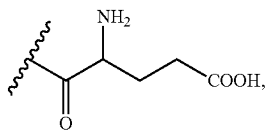

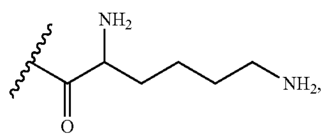

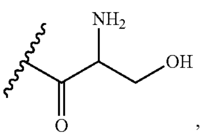
,
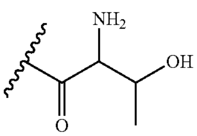
,

-continued

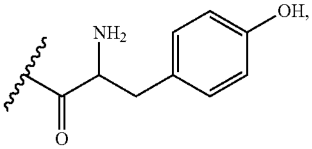

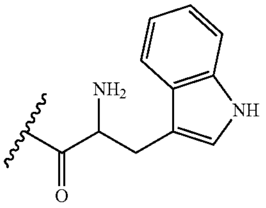
,
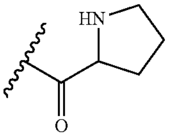
,

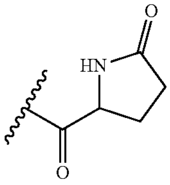
, and
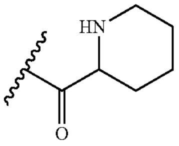
.

In some embodiments, the compound of formula (I) is a compound having the following formula (III):

(III)

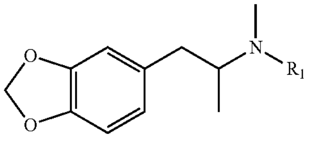

or a pharmaceutically acceptable salt thereof; wherein $R_1$ is selected from the group consisting of:

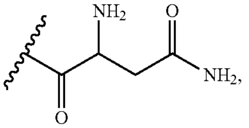

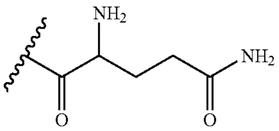
,
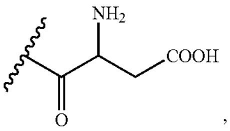
,

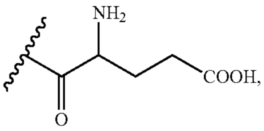

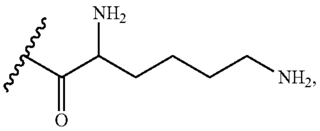

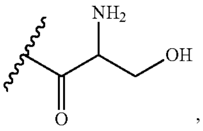
,
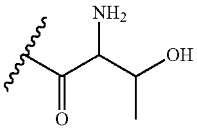
,

-continued

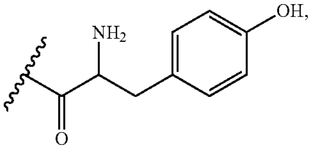

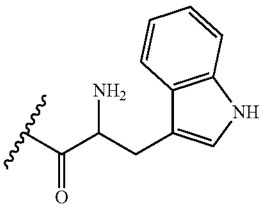
,
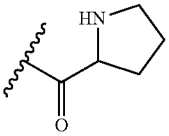
,

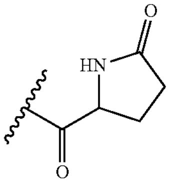
, and
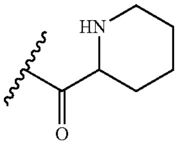
.

In some embodiments, the present disclosure provides a compound of formula (I) or a pharmaceutically acceptable salt thereof, wherein: $R_2$ is —H; $R_3$ is —$CH_3$; $R_4$ is —$OCH_3$—; and $R_1$ is selected from the group consisting of:

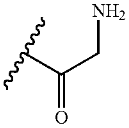
,
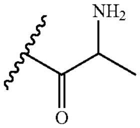
,
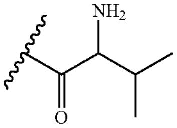
,

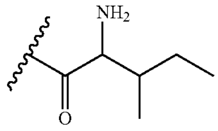
,
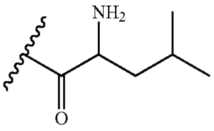
,

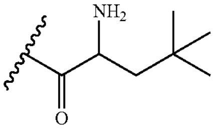
,
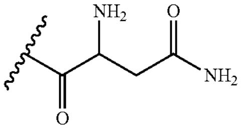
,

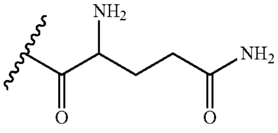
,
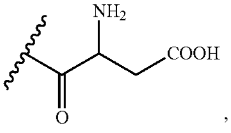
,

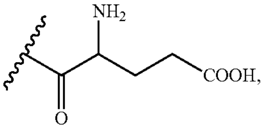

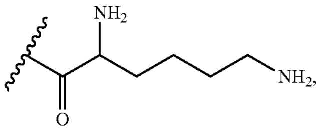

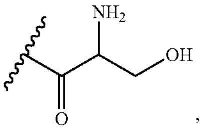
,
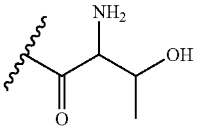
,

-continued

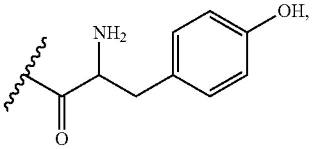

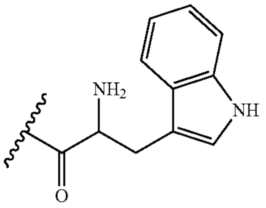, 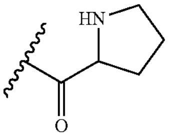,

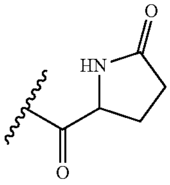, and 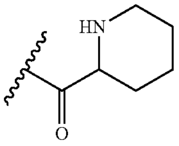.

In some embodiments, the compound of formula (I) is a compound having the following formula (IV):

(IV)

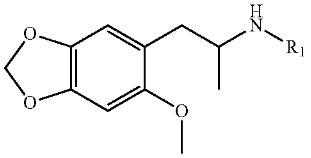

or a pharmaceutically acceptable salt thereof; wherein $R_1$ is selected from the group consisting of:

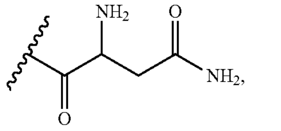

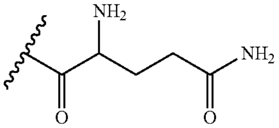, 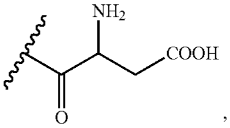,

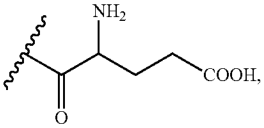

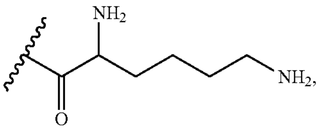

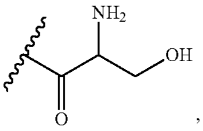, 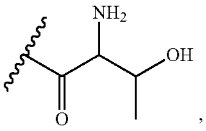,

-continued

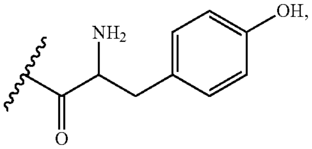

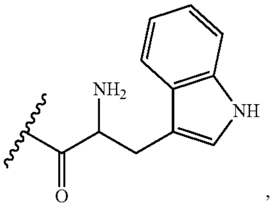, 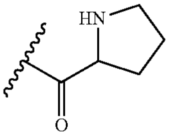,

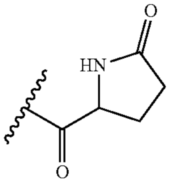, and 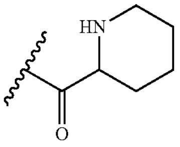.

In some embodiments, the present disclosure provides a compound of formula (I) or a pharmaceutically acceptable salt thereof, wherein: $R_2$ is —H; $R_3$ and $R_4$ are mutually joined to form a group —$CH_2$—; and $R_1$ is selected from the group consisting of:

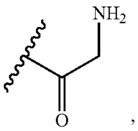, 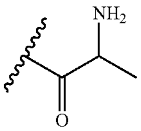, 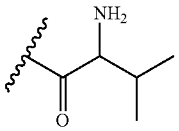,

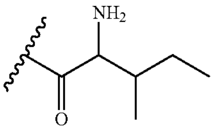, 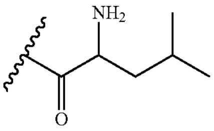,

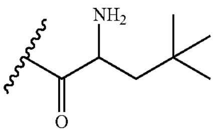, 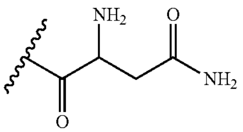,

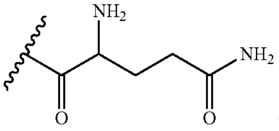, 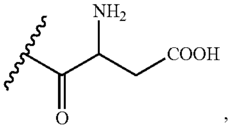,

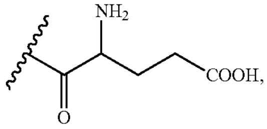

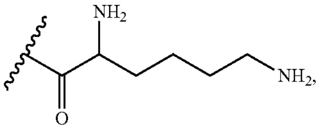

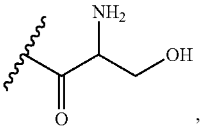, 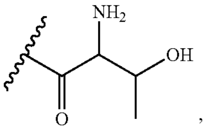,

-continued

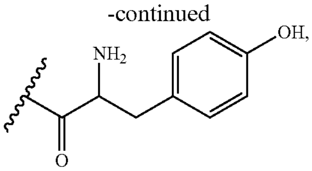

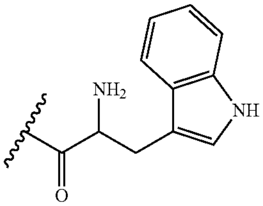
,
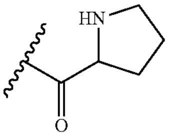
,
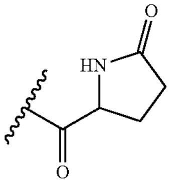
, and
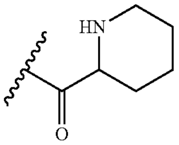
.

In some embodiments, the compound of formula (I) is a compound having the following formula (V):

(V)

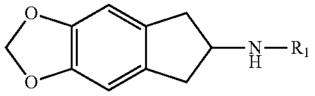

or a pharmaceutically acceptable salt thereof; wherein $R_1$ is selected from the group consisting of:

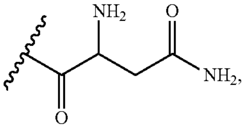

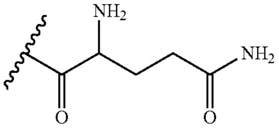
,
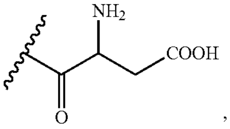
,
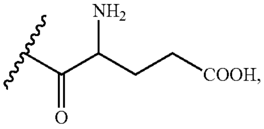

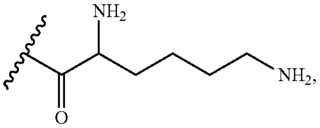

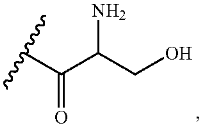
,
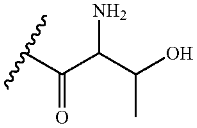
,
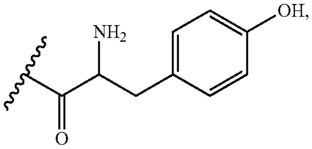

-continued

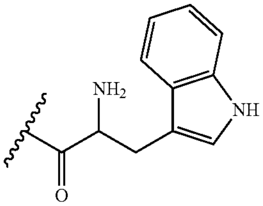
,
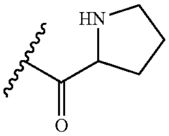
,
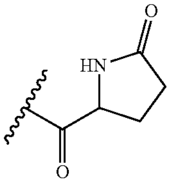
, and
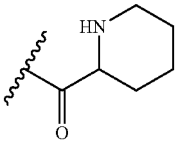
.

In some embodiments, the present disclosure provides a compound of the following formula (Ia) or a pharmaceutically acceptable salt thereof:

(Formula Ia)

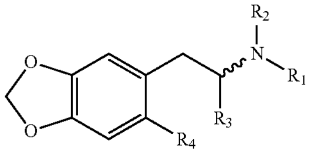

wherein $R_1$ is selected from the group consisting of:

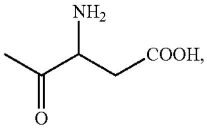

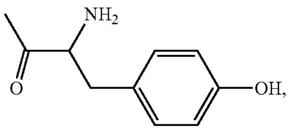

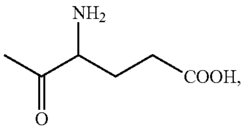

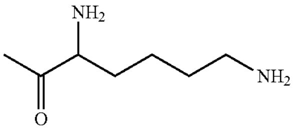
and
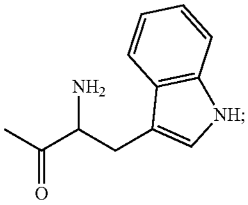

wherein $R_2$ is selected from the group consisting of: —H or —$CH_3$;

wherein $R_3$ is selected from the group consisting of: —$CH_3$ or —$CH_2$—$R_4$; and wherein $R_4$ is selected from the group consisting of: —H or —$OCH_3$ or $R_3$—$CH_2$—.

In some embodiments, the present disclosure provides compounds having the general molecular structure IIa:

(molecular structure IIa)

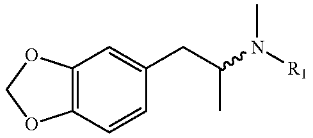

wherein $R_1$ is selected from the group consisting of:

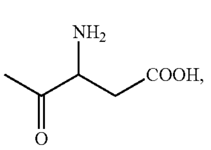

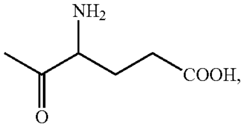

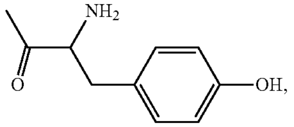

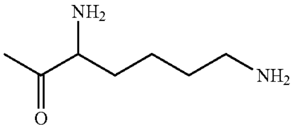

and

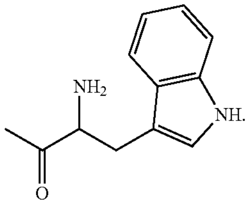

In some embodiments, the present disclosure provides compounds having the following molecular structure IIIa:

(molecular structure IIIa)

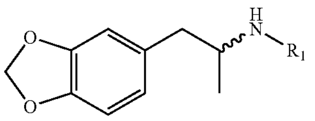

wherein $R_1$ is selected from the group consisting of:

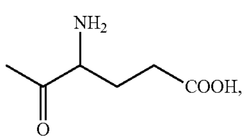

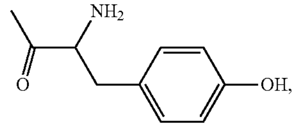

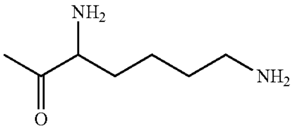

and

-continued

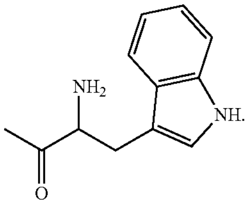

In some embodiments, the present disclosure provides the compounds having the following molecular structure IVa:

(molecular structure IVa)

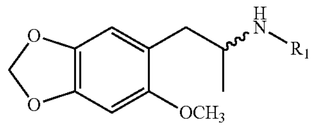

wherein $R_1$ is selected from the group consisting of:

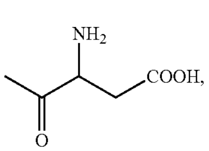

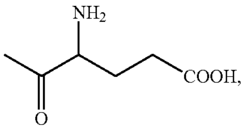

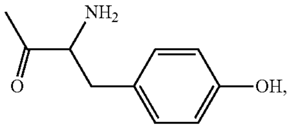

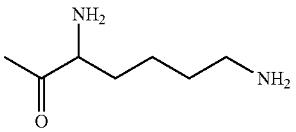

and

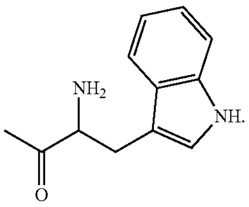

In some embodiments, the present disclosure provides the compounds having the following molecular structure Va:

(molecular structure Va)

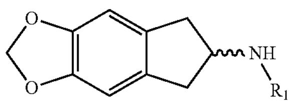

wherein $R_1$ is selected from the group consisting of:

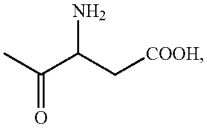,
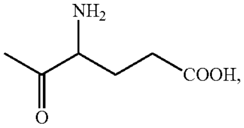,
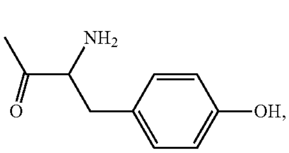,
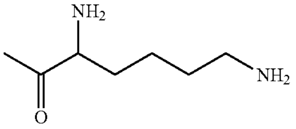 and

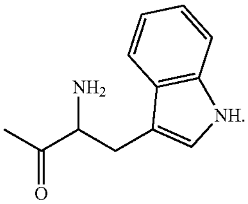.

In accordance with the above, the group $R_1$ in the compounds of formula (I) may be selected from any one of the following amino acid residues:

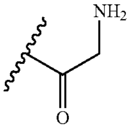
(based on glycine)

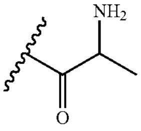
(based on alanine)

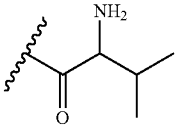
(based on valine)

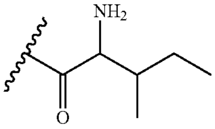
(based on isoleucine)

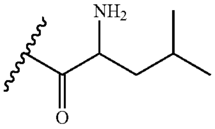
(based on leucine)

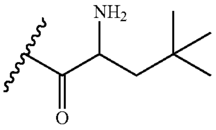
(based on neopentylglycine)

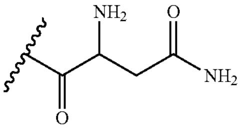
(based on asparagine)

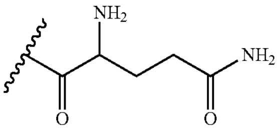
(based on glutamine)

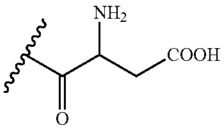
(based on aspartate/aspartic acid)

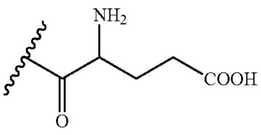
(based on glutamate/glutamic acid)

-continued

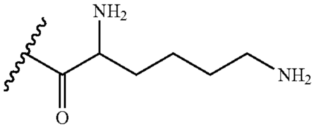
(based on lysine)

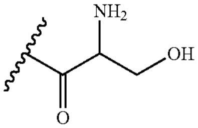
(based on serine)

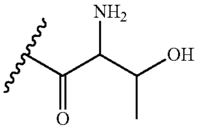
(based on threonine)

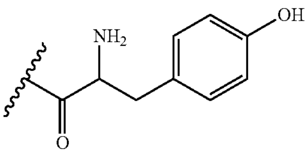
(based on tyrosine)

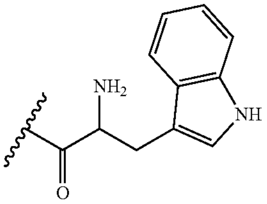 [SMILES: *C(=O)C(N)Cc1c[nH]c2ccccc12]
(based on tryptophan)

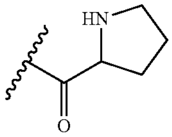
(based on proline)

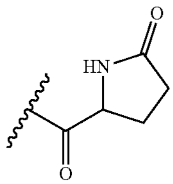
(based on pyroglutamic acid)

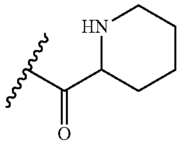
(based on pipecolic acid)

The above-depicted groups $R_1$ may have any configuration. For example, any one of these groups may have the R-configuration or the S-configuration at the chiral carbon atom corresponding to the $C_\alpha$-atom in the respective amino acid. The compound of formula (I) may thus be provided in the form of the corresponding R-isomer or S-isomer, or in the form of any mixture (e.g., a racemic mixture) of these isomers. It is preferred that the above-depicted groups $R_1$ have the S-configuration (at the chiral carbon atom that corresponds to the $C_\alpha$-atom in the respective amino acid).

Compounds in which the aforementioned chiral carbon atom has the R-configuration or the S-configuration can be prepared from the corresponding amino acids having the same configuration (e.g., using an L-amino acid or a D-amino acid). As described herein below, the corresponding amino acid is typically used in protected form, e.g. in the form of N-(9-fluorenylmethyloxycarbonyl)-L-tryptophan, N,N'-di-carbobenzoxy-L-lysine, 1-benzyl-N-carbobenzoxy-L-glutamate, N-carbobenzoxy-L-tyrosine, or 4-benzyl N-carbobenzoxy-L-aspartate. It is preferred that an L-amino acid (typically a protected L-amino acid) is used in the production of the compounds of formula (I).

In some embodiments, the group $R_1$ is selected from

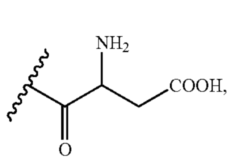,
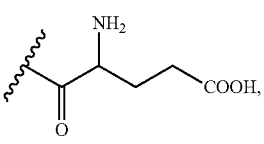,

-continued

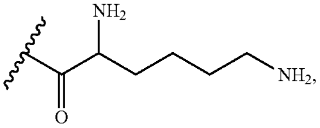,

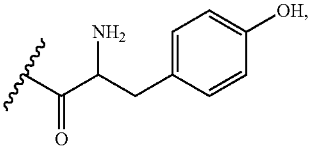, and

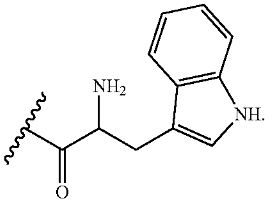 [SMILES: *C(=O)C(N)Cc1c[nH]c2ccccc12].

A particularly preferred group $R_1$ is

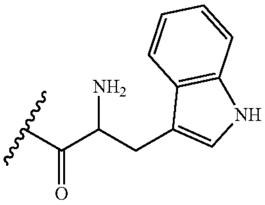

(which preferably has the S-configuration at the chiral carbon atom carrying the —$NH_2$ group). The corresponding compounds of formula (I), having such a group $R_1$, are also referred to herein as "safrylamine tryptophanamides" (or "safrylamine-L-tryptophanamides" if the tryptophan residue as $R_1$ has the L-configuration).

Preferred examples of the compounds of formula (I) according to the invention include any one of the following compounds (as well as pharmaceutically acceptable salts of any of these compounds):

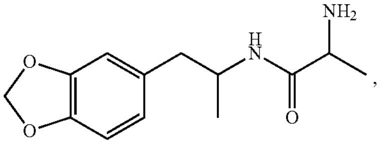,

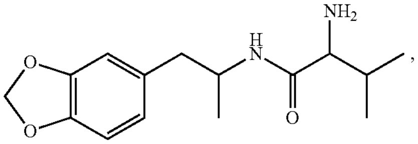,

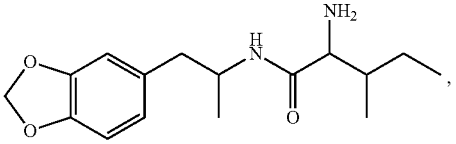,

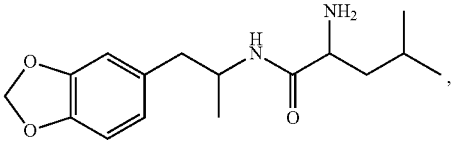,

-continued

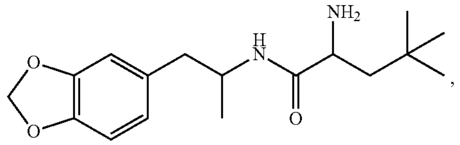,

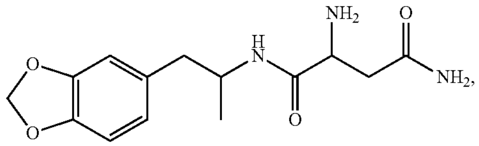,

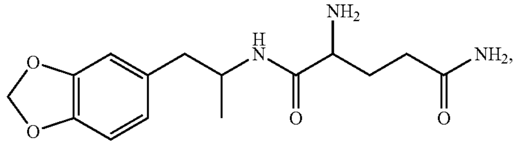,

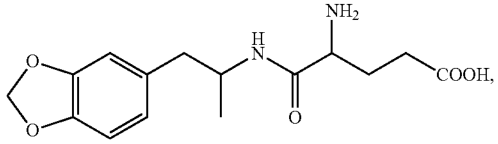,

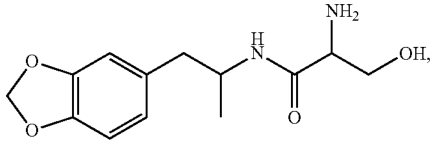,

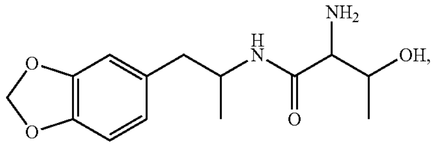,

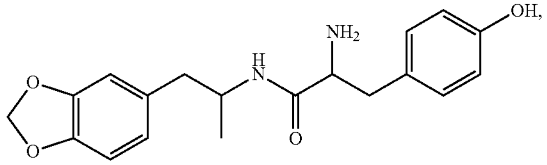,

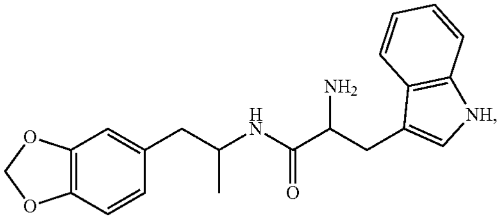,

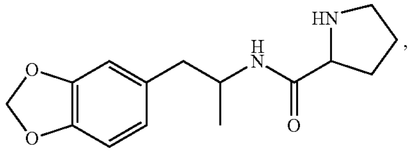,

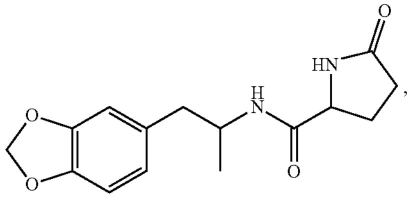,

-continued
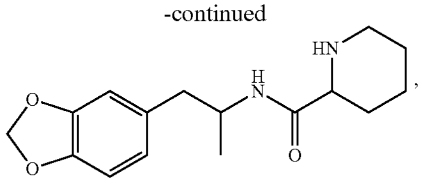
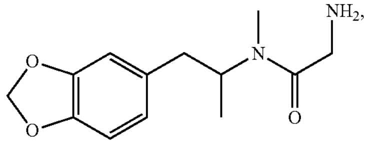
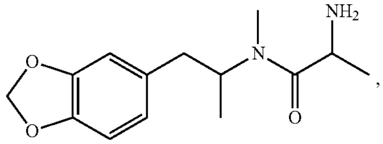
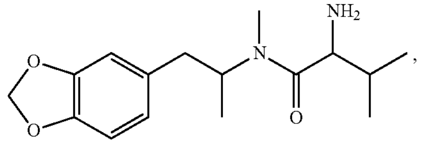
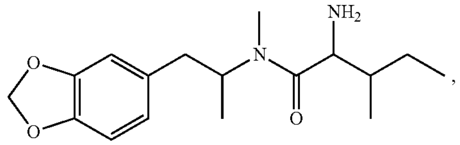
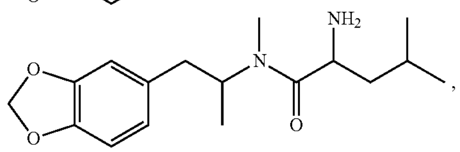
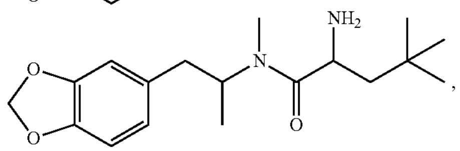
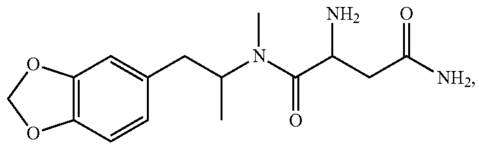
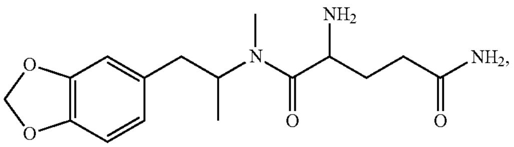
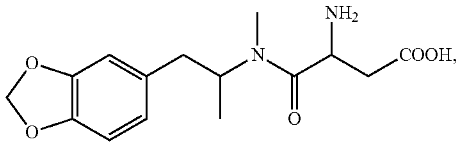
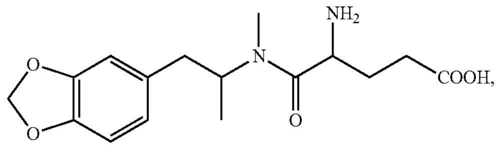
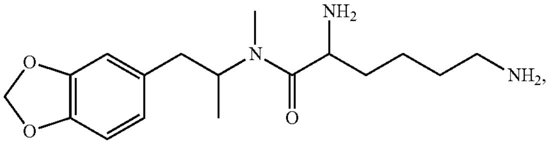
-continued
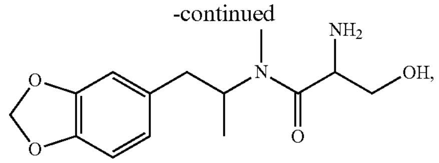
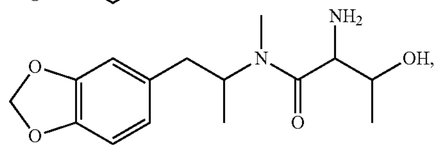
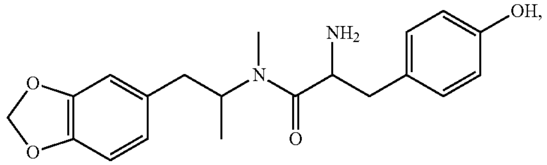
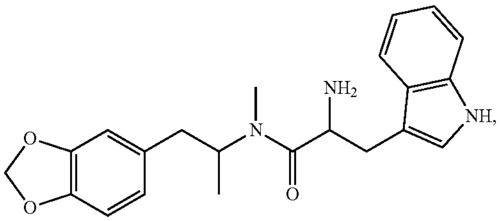
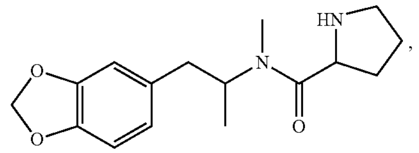
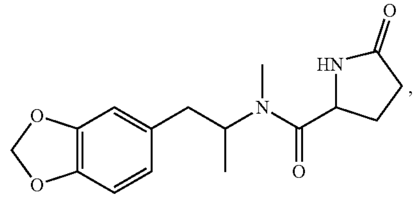
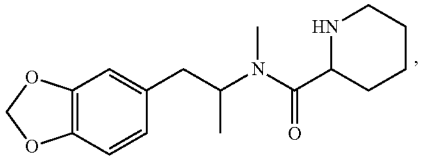
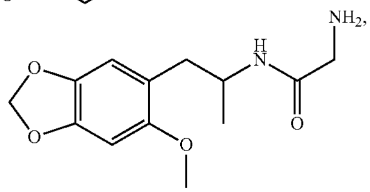
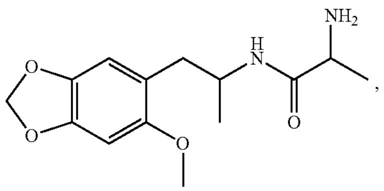
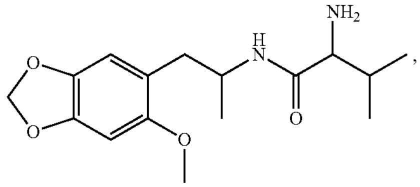

-continued
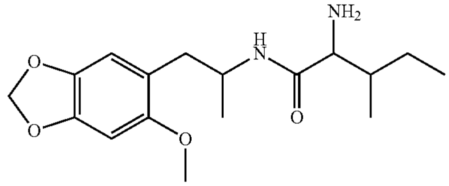
,
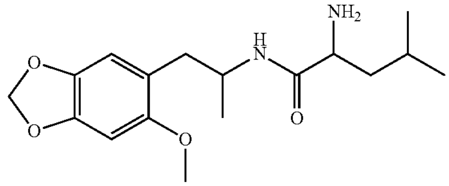
,
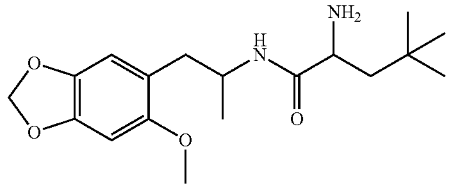
,
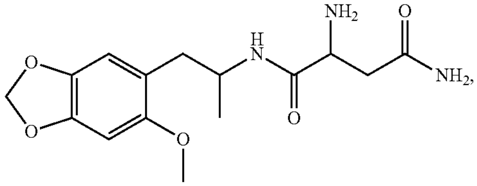
,
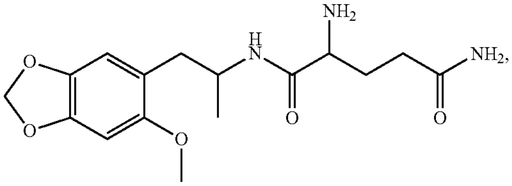
,
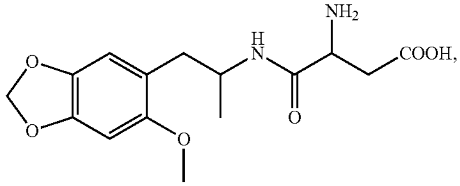
,
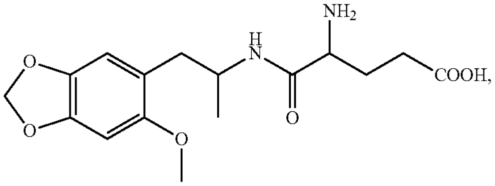
,
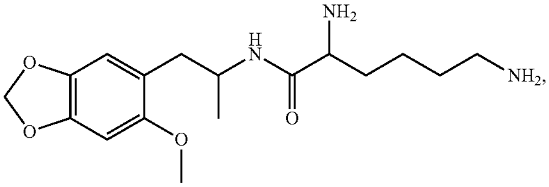
,
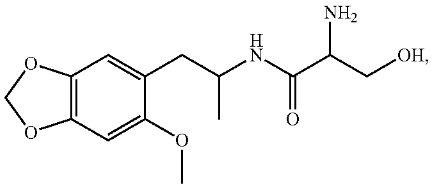
,
-continued
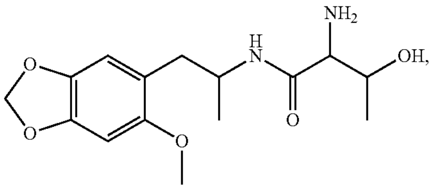
,
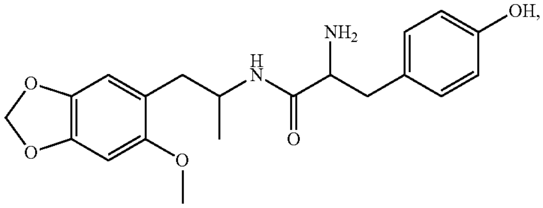
,
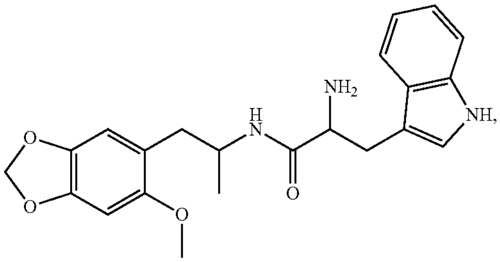
,
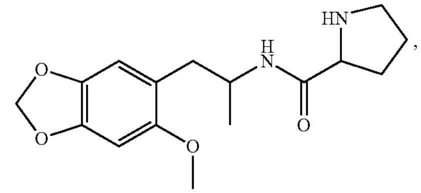
,
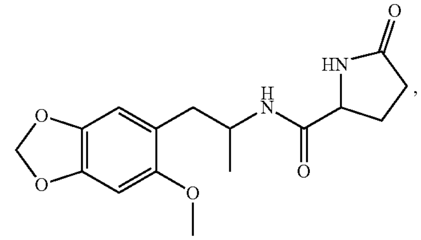
,
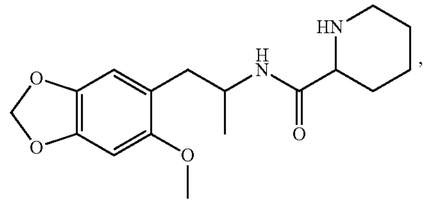
,
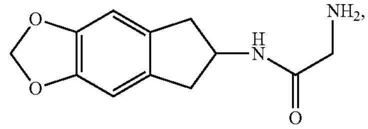
,
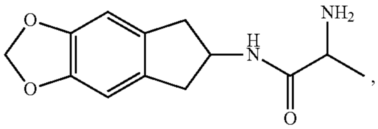
,
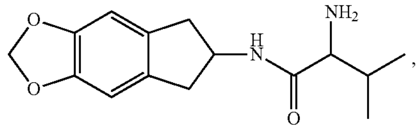
, -continued

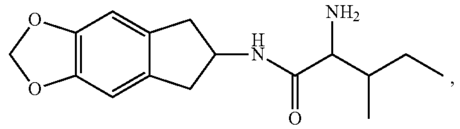,
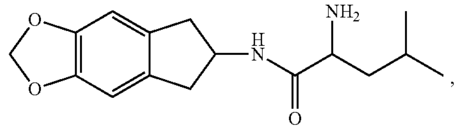,
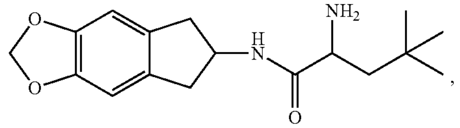,
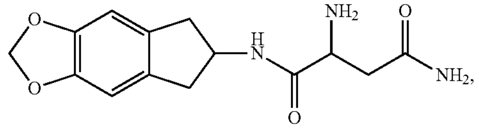,
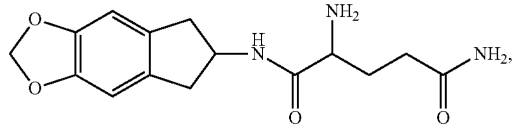,
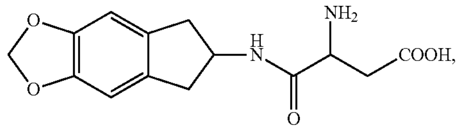,
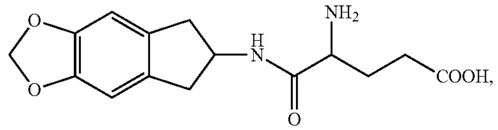,
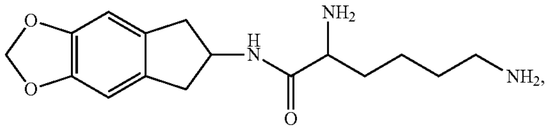,
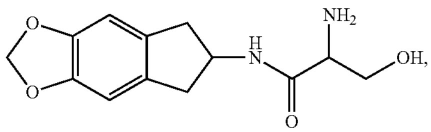,
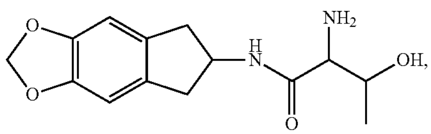,
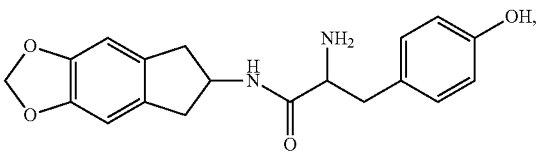,
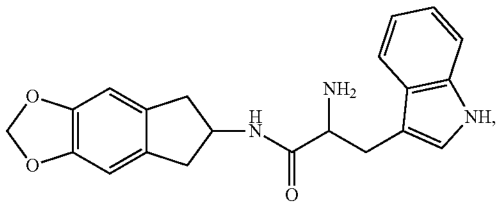, -continued

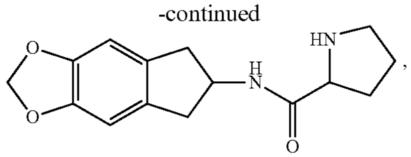,
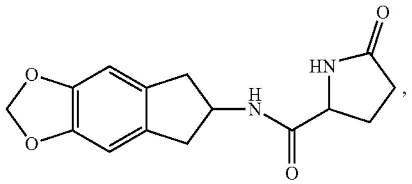, or
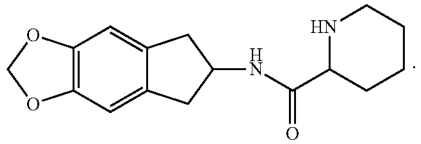.

Further preferred examples of the compounds according to the invention include any one of the compounds described in the examples section, both in non-salt form and in the form of a pharmaceutically acceptable salt of the respective compound.

Due to their specific molecular structure as a "prodrug", i.e. as an active compound to be converted into its active form only within the body, the derivatives presented herein have novel positive pharmacological properties.

Due to their specific molecular structure, the safrylamine peptides according to the present invention are pharmacologically released, taken up and metabolized in the human body with different pharmacokinetics (as compared to the original phenethylamines).

The pharmacological "inactivation" of the actual active compound into the form of a prodrug reduces the potential for abuse because a rapid "flooding" of the active compound is suppressed.

The potential for addiction and the neurotoxic effect of psychotropic substances are often related to a rapid increase of their concentration upon uptake of the substances. Therefore, active compounds leading only to a slow increase from the initial concentration are sought from a pharmaceutical point of view.

The compounds according to the invention exert their effect on the organism only after endogenous metabolization into the actual active safrylamine compounds (such as MDMA, MDA, MMDA-2, or MDAI), whereby delayed pharmacokinetics and a longer-lasting effect are obtained.

The steadier and more uniform release of the active compound in the organism furthermore contributes to reducing side effects.

The "depot effect" resulting from such delayed release is therefore a particular advantage of the present invention.

In further embodiments, by selection of the amino acid derivatives to be used, a beneficial additional pharmacological effect of the safrylamine derivative, besides the retarding effect, can be obtained.

In some embodiments, in the case of the safrylamine-L-aspartate amides, the resulting betaine structure thus provides for better uptake of the safrylamine peptides. In the case of the active compounds of safrylamine-L-tryptophanamide, the amino acid tryptophan, which is released by metabolization, reduces or mitigates the side effect of "serotonin starvation" which may occur in the course of a therapy with MDMA-like active compounds.

The present invention relates to the safrylamine derivatives described herein, including in particular the compounds of formula (I) and likewise the compounds of formula (II), (III), (IV), (V), (Ia), (IIa), (IIIa), (IVa) and (Va), in any form, e.g., in non-salt form or in the form of a salt, particularly a pharmaceutically acceptable salt.

The scope of the present invention thus embraces all pharmaceutically acceptable salt forms of the safrylamine derivatives provided herein, including the compounds of formula (I), which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Further pharmaceutically acceptable salts are described in the literature, e.g., in Stahl PH & Wermuth CG (eds.), "Handbook of Pharmaceutical Salts: Properties, Selection, and Use", Wiley-VCH, 2002 and in the references cited therein. Preferred examples of a pharmaceutically acceptable salt of the safrylamine derivatives according to the invention include, e.g., an oxalate salt, a methanesulfonate (mesylate) salt, or a hydrochloride (HCL) salt.

The scope of the present invention also embraces the safrylamine derivatives provided herein, including the compounds of formula (I), in any hydrated or solvated form, and in any physical form, including any amorphous or crystalline forms.

Moreover, the safrylamine derivatives provided herein, including the compounds of formula (I), may exist in the form of different isomers, in particular stereoisomers (e.g., enantiomers or diastereomers). All such isomers of the compounds provided herein are contemplated as being part of the present invention, either in admixture or in pure or substantially pure form. Thus, for example, the carbon atom carrying the group $R_3$ in formula (I) may constitute a chiral center (particularly if $R_3$ is methyl) and, in that case, may be present in R-configuration or in S-configuration, or as a racemic mixture, and the present invention specifically and individually relates to each one of these possibilities. Any tautomers of the compounds described herein are also embraced by the present invention. As for stereoisomers, the invention embraces the isolated optical isomers of the safrylamine derivatives according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers may also be prepared by using corresponding optically active starting materials in their synthesis, or they may be obtained from corresponding racemates via salt formation with an optically active acid followed by crystallization.

The scope of the invention also embraces safrylamine derivatives of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2H$; also referred to as "D"). Accordingly, the invention also embraces compounds of formula (I) which are enriched in deuterium. Naturally occurring hydrogen is an isotopic mixture comprising about 99.98 mol-% hydrogen-1 ($^1H$) and about 0.0156 mol-% deuterium ($^2H$ or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). The content of deuterium can be determined, e.g., using mass spectrometry or NMR spectroscopy. It is generally preferred that the safrylamine derivatives of formula (I) are not enriched in deuterium. Accordingly, the presence of naturally occurring hydrogen atoms or $^1H$ hydrogen atoms in the compounds of formula (I) is preferred. The invention thus particularly relates to a safrylamine derivative of formula (I) in which all hydrogen atoms are naturally occurring hydrogen atoms or $^1H$ hydrogen atoms.

Methods of Making the Compounds of the Present Disclosure:

In one aspect, the present disclosure provides methods of making the compounds of the present disclosure.

In some embodiments, the present disclosure provides a method for producing compound as described herein, comprising the steps:

a. preparing a solution of a protected amino acid in solvent I;
b. addition of an activating agent dissolved in solvent I under protective gas atmosphere;
c. stirring of the mixture under protective gas atmosphere for at least 2 hours at room temperature;
d. safrylamine (as a free base) dissolved in solvent I is added dropwise under protective gas atmosphere;

-continued

| | |
|---|---|
| e. | stirring of the mixture under protective gas atmosphere for at least 2 hours at room temperature; |
| f. | stopping the reaction by adding 2% ammonia solution; |
| g1. | concentration of the solvent I; |
| g2. | dissolving the residue in solvent II; |
| h. | extraction with 1M HCl, water and saturated saline solution; |
| i. | drying of the organic phase over a desiccant at 40-60° C. and under vacuum; |
| j. | obtaining the crude product; |
| k. | purification of the crude product by recrystallization and/or column chromatography; |
| l. | obtaining the protected safrylamine peptide; |
| m. | deprotection of the protected safrylamine peptide; |
| n. | purification of the safrylamine peptide according to the invention by means of column chromatography; |
| o. | obtaining the safrylamine peptide according to the invention. |

In one embodiment, in step a., between 4.5 mmol and 14.5 mmol of a protected amino acid, which may be selected, e.g., from the group consisting of N-(9-fluorenylmethyloxy-carbonyl)-L-tryptophan, N,N'-di-carbobenzoxy-L-lysine, 1-benzyl-N-carbobenzoxy-L-glutamate, N-carbobenzoxy-L-tyrosine, and 4-benzyl N-carbobenzoxy-L-aspartate, is dissolved in 33 ml up to 100 ml of solvent I, wherein solvent I is, e.g., selected from the group consisting of tetrahydrofuran, dioxane, 2-methyltetrahydrofuran, or dichloromethane.

This can be done, e.g., at a temperature between 5° C. and 40° C., preferably at room temperature (293.15 Kelvin; 20° C.).

The solution obtained is aerated with protective gas.

The term “protective gas”, as used herein, refers to an inert gas, preferably argon. In other embodiments, also a different protective gas can be employed, e.g., elementary gases such as nitrogen, noble gases such as helium, neon, argon, krypton, xenon, and gaseous molecular compounds like sulfur hexafluoride.

In one embodiment, in step b., between 5 mmol and 16 mmol of an activating agent, such as, e.g., 1,1'-carbonyl-diimidazole or a combination of a nitrogen base and a carbodiimide, dissolved in 13 ml to 40 ml of solvent I, are added dropwise. In this case, in preferred embodiments, the nitrogen base is selected from the group consisting of triethylamine, diisopropyl ethylamine, pyridine, and 4-dimethyl aminopyridine. The carbodiimide, which may be added, is preferably selected from the group consisting of dicyclohexyl carbodiimide (DCC), diisopropyl carbodiimide (DIC), 1-ethyl-3-(3-dimethylaminopropyl) carbodiimide (EDC), 1-[biε(dimethylamino)methylene]-1H-1,2,3-triazolo [4,5-b]pyridinium 3-oxide hexafluorophosphate (HATU), or (benzotriazol-1-yloxy)tripyrrolidinophosphonium hexafluorophosphate (PyBOP).

In one embodiment, in step c., the mixture is stirred between 2 and 3 hours at 20-28° C. under protective gas atmosphere.

In one embodiment, in step d., between 5 mmol and 16 mmol of a safrylamine (free base), selected from the group consisting of 3,4-methylenedioxy-N-methylamphetamine (MDMA), 3,4-methylenedioxyamphetamine (MDA), 2-methoxy-4,5-methylenedioxyamphetamine (MMDA-2), and 5,6-methylenedioxy-2-aminoindane (MDAI), dissolved in 8 ml up to 15 ml of solvent I, is added dropwise through a septum.

In one embodiment, in step e., the mixture is stirred between 1 and 3 hours at 20-28° C. under protective gas atmosphere. In one embodiment, it is stirred for at least 0.5 hours and up to 4 hours; and/or at 20° C. under protective gas atmosphere.

In a further embodiment, in step f., the reaction is stopped by adding between 10 ml and 15 ml of 2% ammonia solution.

In a further embodiment, in step g., the mixture is dried, preferably in a rotatory evaporator under vacuum (i.e., at reduced pressure) (step g1.), and is redissolved in solvent II (e.g., in 400 ml to 600 ml of solvent II) (step g2.), wherein solvent II is preferably selected from the group consisting of diethyl ether, methyl-tert-butyl ether, chloroform, and dichloromethane.

In one embodiment, in step h., extraction is performed with between 100 ml and 150 ml of 0.5 molar hydrochloric acid. In one embodiment, subsequent extraction with between 100 ml and 150 ml water is performed. In one embodiment, subsequent extraction with between 100 ml and 150 ml saturated saline solution is performed.

In a further embodiment, in step i., the mixture is dried. Particularly preferred is drying with a desiccant at a temperature between 35° C. and 60° C. and a vacuum (reduced pressure) of 30-60 mbar.

Preferred desiccants are anhydrous calcium chloride, anhydrous sodium carbonate, anhydrous potassium carbonate, anhydrous sodium sulfate, anhydrous magnesium sulfate, or anhydrous calcium sulfate. In one embodiment, the desiccant is anhydrous $MgSO_4$, the temperature is 45° C., and the vacuum (reduced pressure) is 40 mbar.

The crude product obtained in steps a. to j. contains the intermediate product of the protected safrylamine peptide according to the invention.

In a further embodiment, in step k., the crude product is further purified. The purification can be conducted, e.g., by dissolving the crude product in toluene/ethanol at 10:1 with subsequent evaporation at 50° C. and 400 mbar until crystallization and/or column purification over silica using the eluent mixture hexane/ethyl acetate, e.g. in a ratio of 1:1 in one embodiment. Other column materials and eluents known in the art can also be used.

With this method, the intermediate product of step I. can be obtained in yields of more than 60 wt-% (gravimetric determination of the amount of the end product, relative to the starting materials).

In one embodiment, in step m., between 1.6 mmol and 10 mmol of the protected safrylamine peptide are dissolved in 75 ml to 300 ml of solvent I and 3.2 mmol to 20 mmol piperidine are added dropwise. Stirring is conducted for between 2 and 24 hours at 25° C. under protective gas atmosphere. In an alternative embodiment using carbobenzoxy-protected amino acids, cleaving the protective group is carried out via a catalytic hydration using palladium on activated carbon in ethanol as a solvent.

In a further embodiment, in step n., the deprotected safrylamine peptide is further purified. The purification can be conducted by column chromatographic purification over silica using the eluent mixture dichloromethane/methanol with 1% ammonia, e.g., in a ratio of 9:1 in one embodiment. Other column materials and eluents known in the art can also be used.

With this method, in step o., the product can be obtained in yields of more than 80 wt-% (gravimetric determination of the amount of the end product, relative to the intermediate product).

Further details on the method of production are provided in the examples and will be apparent to the person skilled in the art. The method of production allows producing the compounds according to the invention in high purity.

The safrylamine derivatives of formula (I), wherein $R_1$ is a pyroglutamic acid group, can be prepared using the method of production described herein above. Alternatively, any of these pyroglutamic acid compounds can also be obtained by preparing the corresponding glutamate compound (wherein $R_1$ is a glutamate/glutamic acid group) and subjecting the glutamate compound to a coupling agent (e.g., dicyclohexyl carbodiimide (DCC) in a solvent such as N,N-dimethylformamide (DMF)) to induce an intramolecular cyclization, which yields the desired pyroglutamic acid compound.

Pharmaceutical Compositions:

The present invention provides a pharmaceutical/pharmacological composition comprising at least one safrylamine derivative according to the invention (particularly a compound of formula (I) or a pharmaceutically acceptable salt thereof) and optionally one or more pharmaceutically acceptable excipients. The invention likewise relates to the safrylamine derivatives provided herein (particularly a compound of formula (I) or a pharmaceutically acceptable salt thereof), or the aforementioned pharmaceutical composition, for use in therapy (or for use as a medicament).

The safrylamine derivatives provided herein, including the compounds of formula (I), may be administered as compounds per se or may be formulated as pharmaceutical/pharmacological compositions or medicaments. The pharmaceutical compositions/medicaments may optionally comprise one or more pharmaceutically acceptable excipients, such as carriers, diluents, fillers, disintegrants, lubricating agents, binders, colorants, pigments, stabilizers, preservatives, and/or antioxidants.

The pharmaceutical compositions can be formulated by techniques known to the person skilled in the art, such as the techniques published in "Remington: The Science and Practice of Pharmacy", Pharmaceutical Press, $22^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

Methods of Treatment:

The invention further relates to a safrylamine derivative as described herein, particularly a compound of formula (I), which may be present in non-salt form or in the form of a pharmaceutically acceptable salt, or a pharmaceutical composition comprising at least one safrylamine derivative, for use in the treatment of a serotonin 5-$HT_{2A}$ receptor associated disease/disorder. In particular, the invention relates to a safrylamine derivative or a pharmaceutical composition, as described herein, for use in the treatment of an anxiety disorder, attention deficit hyperactivity disorder (ADHD), posttraumatic stress disorder (PTSD), depression, cluster headache, a condition associated with cancer, diminished drive, burn-out, bore-out, migraine, Parkinson's disease, pulmonary hypertension, schizophrenia, an eating disorder, nausea, or vomiting.

The invention also refers to the use of a safrylamine derivative as described herein, particularly a compound of formula (I) or a pharmaceutically acceptable salt thereof, in the manufacture of a medicament for the treatment of a serotonin 5-$HT_{2A}$ receptor associated disease/disorder, preferably for the treatment of an anxiety disorder, attention deficit hyperactivity disorder (ADHD), posttraumatic stress disorder (PTSD), depression, cluster headache, a condition associated with cancer, diminished drive, burn-out, bore-out, migraine, Parkinson's disease, pulmonary hypertension, schizophrenia, an eating disorder, nausea, or vomiting.

Moreover, the invention provides a method of treating a disease/disorder, particularly a serotonin 5-$HT_{2A}$ receptor associated disease/disorder, in a subject in need thereof, the method comprising administering a therapeutically effective amount of the safrylamine derivative according to the invention, particularly a compound of formula (I) or a pharmaceutically acceptable salt thereof, to said subject. It is preferred that the disease/disorder to be treated is an anxiety disorder, attention deficit hyperactivity disorder (ADHD), posttraumatic stress disorder (PTSD), depression, cluster headache, a condition associated with cancer, diminished drive, burn-out, bore-out, migraine, Parkinson's disease, pulmonary hypertension, schizophrenia, an eating disorder, nausea, or vomiting.

In principle, the safrylamine derivatives of formula (I) or the corresponding pharmaceutical compositions may be administered to a subject by any convenient route of administration. Various routes for administering pharmaceutical agents are known in the art and include, inter alia, oral (e.g., as a tablet, capsule, ovule, elixir, or as an ingestible solution or suspension), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, or vaginal administration.

It is particularly preferred that the safrylamine derivatives according to the invention (or corresponding pharmaceutical compositions) are administered orally, sublingually, or nasally (e.g., as a nasal spray or as nose drops). Suitable dosage forms for oral administration include, e.g., coated or uncoated tablets, soft gelatin capsules, hard gelatin capsules, lozenges, troches, solutions, emulsions, suspensions, syrups, elixirs, powders or granules for reconstitution, dispersible powders or granules, medicated gums, chewing tablets, or effervescent tablets. For oral administration, the safrylamine derivatives or pharmaceutical compositions are preferably administered by oral ingestion, particularly by swallowing. The compounds or pharmaceutical compositions can thus be administered to pass through the mouth into the gastrointestinal tract, which can also be referred to as “oral-gastrointestinal” administration.

The subject or patient to be treated in accordance with the present invention may be an animal (e.g., a non-human animal). Preferably, the subject/patient is a mammal. More preferably, the subject/patient is a human (e.g., a male human or a female human) or a non-human mammal. Most preferably, the subject/patient to be treated in accordance with the invention is a human.

In this specification, a number of documents including patent applications/patents are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

The invention will now be described by reference to the following examples which are merely illustrative and are not to be construed as a limitation of the scope of the present invention.

EXAMPLES

Example 1: Method of Production of 3,4-methylenedioxy-N-methylamphetamine-N'-L-tryptophanamide N-(9-Fluorenylmethyloxycarbonyl)-L-tryptophan (8.7 mmol/3.71 g) was dissolved in tetrahydrofuran (60 ml) at 25° C. and aerated with argon.

1,1'-Carbonyldiimidazole (9.6 mmol/1.55 g) was dissolved in tetrahydrofuran (25 ml) and added dropwise through the septum.

The reaction mixture was stirred for 90 min at 25° C.

3,4-Methylenedioxy-N-methylamphetamine (9.6 mmol/1.85 g) was dissolved in tetrahydrofuran (10 ml) and added dropwise through the septum.

Stirring was conducted for 2 hours under argon at 25° C.

The reaction was stopped with 2% ammonia solution (10 ml) and the reaction mixture was distilled off on the rotary evaporator.

The residue was added to dichloromethane (300 ml) and extracted with 0.5 M hydrochloric acid (100 ml), water (100 ml) and saturated saline solution (100 ml).

The organic phase was dried over magnesium sulfate and evaporated. In this way, 4.1 g of a yellowish oil was obtained.

The crude product was recrystallized in a solvent mixture of toluene/ethanol in a ratio of 10:1 at 70° C. Thereby, 2.0 g were obtained as a pure colorless solid (=intermediate product).

Cleavage of the Protective Group:

The intermediate product (3.3 mmol/2.0 g) was dissolved in tetrahydrofuran (100 ml) at 25° C.

Piperidine (6.6 mmol/0.56 g) was added dropwise and was aerated with argon.

Stirring was conducted for 20 hours at 25° C. and the completed deprotection was detected by means of thin layer chromatography.

The reaction mixture was concentrated on the rotary evaporator at 42° C. and subsequently dried at up to 10 mbar. The obtained crude product was chromatographed over 200 g silica using the eluent mixture dichloromethane/methanol with 1% ammonia in a ratio of 9:1. As a result, 1.60 g of a colorless solid was obtained.

Example 2: Method of Production of 3,4-methylenedioxyamphetamine-N-L-tryptophanamide N-(9-Fluorenylmethyloxycarbonyl)-L-tryptophan (14.5 mmol/6.18 g) was dissolved in tetrahydrofuran (100 ml) at 25° C. and aerated with argon.

1,1'-Carbonyldiimidazole (16 mmol/2.59 g) was dissolved in tetrahydrofuran (40 ml) and added dropwise through the septum.

The reaction mixture was stirred for 2 hours at 25° C.

3,4-Methylenedioxyamphetamine (9.6 mmol/1.85 g) was dissolved in tetrahydrofuran (10 ml) and added dropwise through the septum.

Stirring was conducted for 2 hours under argon at 25° C.

The reaction was stopped with 2% ammonia solution (13 ml) and the reaction mixture was distilled off on the rotary evaporator.

The residue was added to dichloromethane (400 ml) and extracted with 0.5 M hydrochloric acid (150 ml), water (150 ml) and saturated saline solution (150 ml).

The organic phase was dried over magnesium sulfate and evaporated. In this way, 9.2 g of a colorless solid was obtained.

The crude product was recrystallized in a solvent mixture toluene/ethanol in a ratio of 10:1 at 70° C. This yielded 6.1 g as a pure colorless solid (=intermediate product).

Cleavage of the Protective Group:

The intermediate product (10 mmol/5.87 g) was dissolved in tetrahydrofuran (300 ml) at 25° C.

Piperidine (20 mmol/1.70 g) was added dropwise and aerated with argon.

Stirring was conducted for 20 hours at 25° C. and the completed deprotection was detected by means of thin layer chromatography.

The reaction mixture was concentrated on the rotary evaporator at 42° C. and subsequently dried at up to 10 mbar. The obtained crude product was chromatographed over 300 g silica using the eluent mixture dichloromethane/methanol with 1% ammonia in a ratio of 9:1. This yielded 3.20 g of a colorless solid.

Example 3: Method of Production of 2-methoxy-4,5-methylenedioxyamphetamine-N-L-tryptophanamide N-(9-Fluorenylmethyloxycarbonyl)-L-tryptophan (9 mmol/3.83 g) was dissolved in tetrahydrofuran (70 ml) at 25° C. and aerated with argon.

1,1'-Carbonyldiimidazole (10 mmol/1.62 g) was dissolved in tetrahydrofuran (30 ml) and added dropwise through the septum.

The reaction mixture was stirred for 2 hours at 25° C.

2-Methoxy-4,5-methylenedioxyamphetamine (10 mmol/2.09 g) was dissolved in tetrahydrofuran (15 ml) and added dropwise through the septum.

Following stirring for one hour under argon at 25° C., an almost complete conversion of the reactant was detected by means of thin layer chromatography. Stirring was continued for another 19 hours.

The reaction was stopped with 2% ammonia solution (10 ml) and the reaction mixture was distilled off on the rotary evaporator.

The residue was added to dichloromethane (400 ml) and extracted with 0.5 M hydrochloric acid (150 ml), water (150 ml) and saturated saline solution (150 ml).

The organic phase was dried over magnesium sulfate and evaporated. In this way, 5.0 g of an ochre-colored solid was obtained.

The crude product was chromatographed over 300 g silica using the eluent mixture hexane/ethyl acetate with 1% triethylamine in a ratio of 1:1. This yielded 1.80 g of a colorless solid.

Cleavage of the Protective Group:

The intermediate product (2.9 mmol/1.80 g) was dissolved in tetrahydrofuran (180 ml) at 25° C.

Piperidine (5.8 mmol/493 g) was added dropwise and aerated with argon.

Stirring was conducted for 20 hours at 25° C. and the completed deprotection was detected by means of thin layer chromatography.

The reaction mixture was concentrated on the rotary evaporator at 42° C. and subsequently dried at up to 10 mbar. The obtained crude product was chromatographed over 300 g silica using the eluent mixture dichloromethane/methanol with 1% ammonia in a ratio of 9:1. This yielded 1.01 g of a colorless solid.

Example 4: Method of Production of 5,6-methylenedioxy-2-aminoindane-N-L-tryptophanamide N-(9-Fluorenylmethyloxycarbonyl)-L-tryptophan (4.5 mmol/1.92 g) was dissolved in tetrahydrofuran (35 ml) at 25° C. and aerated with argon.

1,1'-Carbonyldiimidazole (5 mmol/810 g) was dissolved in tetrahydrofuran (13 ml) and added dropwise through the septum.

The reaction mixture was stirred for 2 hours at 25° C.

5,6-Methylenedioxy-2-aminoindane (5 mmol/885 mg) was dissolved in tetrahydrofuran (10 ml) and added dropwise through the septum.

Following stirring for one hour under argon at 25° C., an almost complete conversion of the reactant was detected by means of thin layer chromatography. Stirring was continued for another 1 hour at 25° C.

The reaction was stopped with 2% ammonia solution (13 ml) and the reaction mixture was distilled off on the rotary evaporator.

The residue was added to dichloromethane (400 ml) and extracted with 0.5 M hydrochloric acid (150 ml), water (150 ml) and saturated saline solution (150 ml).

The organic phase was dried over magnesium sulfate and evaporated. This yielded 1.90 g of a colorless solid.

The crude product was chromatographed over 100 g silica using the eluent mixture hexane/ethyl acetate with 1% triethylamine in a ratio of 5:3. This yielded 970 mg of a colorless solid.

Cleavage of the Protective Group:

The intermediate product (1.6 mmol/970 mg) was dissolved in tetrahydrofuran (180 ml) at 25° C.

Piperidine (3.2 mmol/275 mg) was added dropwise and aerated with argon.

Stirring was conducted for 20 hours at 25° C. and the completed deprotection was detected by means of thin layer chromatography.

The reaction mixture was concentrated on the rotary evaporator at 42° C. and subsequently dried at up to 10 mbar. The obtained crude product was chromatographed over 70 g silica using the eluent mixture dichloromethane/methanol with 1% ammonia in a ratio of 9:1. This yielded 540 mg of a colorless solid.

Example 5: Method of Production of the safrylamin-N-L-lysinamides

The method of production of the safrylamin-N-L-lysinamides is analogous to the method of production of 3,4-methylenedioxyamphetamine-N-L-tryptophanamide (see Example 2).

It comprises the steps:

| | |
|---|---|
| a. | preparing a solution of N,N'-di-carbobenzoxy-L-lysine in solvent I; |
| b. | addition of an activating agent dissolved in solvent I under protective gas atmosphere; |
| c. | stirring of the mixture under protective gas atmosphere for at least 2 hours at room temperature; |
| d. | safrylamine (as a free base) dissolved in solvent I is added dropwise under protective gas atmosphere; |
| e. | stirring of the mixture under protective gas atmosphere for at least 2 hours at room temperature; |
| f. | stopping the reaction by adding 2% ammonia solution; |
| g1. | concentration of the solvent I; |
| g2. | dissolving the residue in solvent II; |
| h. | extraction with 1M HCl, water and saturated saline solution; |
| i. | drying of the organic phase over a desiccant at 40-60° C. and under vacuum; |
| j. | obtaining the crude product; |
| k. | purification of the crude product by recrystallization and/or column chromatography; |
| l. | obtaining the carbobenzoxy-protected safrylamine-N-L-lysinamide; |
| m. | cleaving the protective groups of the carbobenzoxy-protected safrylamine-N-L-lysinamide by hydration using palladium on activated carbon in ethanol; |
| n. | purification of the safrylamine-N-L-lysinamide according to the invention by means of column chromatography using the eluent mixture dichloromethane/methanol with 1% ammonia in a ratio of 9:1; |
| o. | obtaining the safrylamine-N-L-lysinamide according to the invention. |

Example 6: Method of Production of the safrylamine-N-L-aspartate Amides

The method of production of the safrylamine-N-L-aspartate amides is analogous to the method of production of 3,4-methylenedioxyamphetamine-N-L-tryptophanamide (see Example 2).

It comprises the steps:

a. preparing a solution of 4-benzyl N-carbobenzoxy-L-aspartate in solvent I;
b. addition of an activating agent dissolved in solvent I under protective gas atmosphere;
c. stirring of the mixture under protective gas atmosphere for at least 2 hours at room temperature;
d. safrylamine (as a free base) dissolved in solvent I is added dropwise under protective gas atmosphere;
e. stirring of the mixture under protective gas atmosphere for at least 2 hours at room temperature;
f. stopping the reaction by adding 2% ammonia solution;
g1. concentration of the solvent I;
g2. dissolving the residue in solvent II;
h. extraction with 1M HCl, water and saturated saline solution;
i. drying of the organic phase over a desiccant at 40-60° C. and under vacuum;
j. obtaining the crude product;
k. purification of the crude product by recrystallization and/or column chromatography;
l. obtaining the carbobenzoxy/benzyl-protected safrylamine-N-L-aspartate amide;
m. cleaving the protective groups of the carbobenzoxy/benzyl-protected safrylamine-N-L-aspartate amide by hydration using palladium on activated carbon in ethanol;
n. purification of the safrylamine-N-L-aspartate amide according to the invention by means of column chromatography using the eluent mixture dichloromethane/methanol with 1% ammonia in a ratio of 9:1;
o. obtaining the safrylamine-N-L-aspartate amide according to the invention.

Example 7: Method of Production of the safrylamine-N-L-glutamate Amides

The method of production of the safrylamine-N-L-glutamate amides is analogous to the method of production of 3,4-methylenedioxyamphetamine-N-L-tryptophanamide (see Example 2).

It comprises the steps:

a. preparing a solution of 1-benzyl N-carbobenzoxy-L-glutamate in solvent I;
b. addition of an activating agent dissolved in solvent I under protective gas atmosphere;
c. stirring of the mixture under protective gas atmosphere for at least 2 hours at room temperature;
d. safrylamine (as a free base) dissolved in solvent I is added dropwise under protective gas atmosphere;
e. stirring of the mixture under protective gas atmosphere for at least 2 hours at room temperature;
f. stopping the reaction by adding 2% ammonia solution;
g1. concentration of the solvent I;
g2. dissolving the residue in solvent II;
h. extraction with 1M HCl, water and saturated saline solution;
i. drying of the organic phase over a desiccant at 40-60° C. and under vacuum;
j. obtaining the crude product;
k. purification of the crude product by recrystallization and/or column chromatography;
l. obtaining the carbobenzoxy/benzyl-protected safrylamine-N-L-glutamate amide;
m. cleaving the protective groups of the carbobenzoxy/benzyl-protected safrylamine-N-L-glutamate amide by hydration using palladium on activated carbon in ethanol;
n. purification of the safrylamine-N-L-glutamate amide according to the invention by means of column chromatography using the eluent mixture dichloromethane/methanol with 1% ammonia in a ratio of 9:1;
o. obtaining the safrylamine-N-L-glutamate amide according to the invention.

Example 8: Method of Production of the safrylamine-N-L-tyrosinamides

The method of production of the safrylamine-N-L-tyrosinamides is analogous to the method of production of 3,4-methylenedioxyamphetamine-N-L-tryptophanamide (see Example 2).

It comprises the steps:

a. preparing a solution of N-carbobenzoxy-L-tyrosine in solvent I;
b. addition of an activating agent dissolved in solvent I under protective gas atmosphere;
c. stirring of the mixture under protective gas atmosphere for at least 2 hours at room temperature;
d. safrylamine (as a free base) dissolved in solvent I is added dropwise under protective gas atmosphere;
e. stirring of the mixture under protective gas atmosphere for at least 2 hours at room temperature;
f. stopping the reaction by adding 2% ammonia solution;
g1. concentration of the solvent I;
g2. dissolving the residue in solvent II;
h. extraction with 1M HCl, water and saturated saline solution;
i. drying of the organic phase over a desiccant at 40-60° C. and under vacuum;
j. obtaining the crude product;
k. purification of the crude product by recrystallization and/or column chromatography;
l. obtaining the carbobenzoxy-protected safrylamine-N-L-tyrosinamide;

-continued

| | |
|---|---|
| m. | cleaving the protective group of the carbobenzoxy-protected safrylamine-N-L-tyrosinamide by hydration using palladium on activated carbon in ethanol; |
| n. | purification of the safrylamine-N-L-tyrosinamide according to the invention by means of column chromatography using the eluent mixture dichloromethane/methanol with 1% ammonia in a ratio of 9:1; |
| o. | obtaining the safrylamine-N-L-tyrosinamide according to the invention. |

Example 9: Method of Production of 3,4-methylenedioxy-N-methylamphetamine-N'-L-glycinamide N-benzyloxycarbonyl-glycine (4.4 mmol/920 mg) was dissolved in tetrahydrofuran (12 ml) at 25° C. and aerated with argon.

1,1'-Carbonyldiimidazole (4.8 mmol/778 mg) was dissolved in tetrahydrofuran (8 ml) and added dropwise through the septum.

The reaction mixture was stirred for 120 min at 25° C.

3,4-Methylenedioxy-N-methylamphetamine (4.8 mmol/926 mg) was dissolved in tetrahydrofuran (5 ml) and added dropwise through the septum.

Stirring was conducted for 20 hours under argon at 25° C.

The crude reaction mixture was filtered through a silica plug and rinsed several times with tetrahydrofuran and the collected filtrate was distilled off on the rotary evaporator.

In this way, 1.78 g of a yellowish oil was obtained.

Cleavage of the Protective Group:

In a Schlenk-flask the crude intermediate product (4.4 mmol/1.68 g) was dissolved in ethanol (50 ml) at 25° C.

Palladium on carbon (5%/210 mg) was added and was charged with hydrogen.

Stirring was conducted for 1 hour at 25° C. and the completed deprotection was detected by means of thin layer chromatography.

The reaction mixture was filtered through a silica-plug and the resulting filtrate was distilled off on the rotary evaporator and subsequently dried at up to 10 mbar.

In this way, 980 mg of the title compound as a colorless oil was obtained.

Example 10: Method of Production of 3,4-methylenedioxy-amphetamine-N-L-glycinamide N-benzyloxycarbonyl-glycine (5.4 mmol/1.14 g) was dissolved in tetrahydrofuran (12 ml) at 25° C. and aerated with argon.

1,1'-Carbonyldiimidazole (6 mmol/972 mg) was dissolved in tetrahydrofuran (10 ml) and added dropwise through the septum.

The reaction mixture was stirred for 120 min at 25° C.

3,4-Methylenedioxy-amphetamine (6 mmol/1.07 g) was dissolved in tetrahydrofuran (7 ml) and added dropwise through the septum.

Stirring was conducted for 4 hours under argon at 25° C.

The crude reaction mixture was filtered through a silica plug and rinsed several times with tetrahydrofuran and the collected filtrate was distilled off on the rotary evaporator.

In this way, 2.18 g of a yellowish oil was obtained.

Cleavage of the Protective Group:

In a Schlenk-flask the crude intermediate product (5.34 mmol/1.98 g) was dissolved in ethanol (90 ml) at 25° C.

Palladium on carbon (5%/500 mg) was added and was charged with hydrogen.

Stirring was conducted for 1 hour at 25° C. and the completed deprotection was detected by means of thin layer chromatography.

The reaction mixture was filtered through a silica-plug and the resulting filtrate was distilled off on the rotary evaporator and subsequently dried at up to 10 mbar.

In this way, 1.26 g of the title compound as a colorless oil was obtained.

Example 11: Method of Production of 3,4-methylenedioxy-amphetamine-N-L-glutamic Acid Amide 5-benzyl-N-benzyloxycarbonyl-glutamate (5.4 mmol/1.14 g) was dissolved in tetrahydrofuran (12 ml) at 25° C. and aerated with argon.

1,1'-Carbonyldiimidazole (6 mmol/972 mg) was dissolved in tetrahydrofuran (10 ml) and added dropwise through the septum.

The reaction mixture was stirred for 120 min at 25° C.

3,4-Methylenedioxy-amphetamine (6 mmol/1.07 g) was dissolved in tetrahydrofuran (10 ml) and added dropwise through the septum.

Stirring was conducted for 4 hours under argon at 25° C.

The crude reaction mixture was filtered through a silica plug and rinsed several times with tetrahydrofuran and the collected filtrate was distilled off on the rotary evaporator.

In this way, 2.36 g of a white powder was obtained.

Cleavage of the Protective Group:

In a Schlenk-flask the crude intermediate product (4.0 mmol/2.13 g) was dissolved in a mixture of dioxane/acetic acid (70 ml/20 ml) at 25° C.

Palladium on carbon (5%/200 mg) was added and was charged with hydrogen.

Stirring was conducted for 4 hours at 25° C. and the completed deprotection was detected by means of thin layer chromatography.

The reaction mixture was filtered through a silica-plug and the resulting filtrate was distilled off on the rotary evaporator and subsequently dried at up to 10 mbar.

In order to remove impurities of byproducts, the resulting residue was dissolved in water (120 ml) and washed twice with dichloromethane (30 ml). The aqueous solution was gently distilled off on the rotary evaporator at 35° C.

After drying at high vacuum, 890 mg of the title compound as a colorless vitreous solid was obtained.

Example 12: Solubility and Lipophilicity of Novel Compounds

Introduction

Two novel compounds according to the invention, i.e. 5,6-methylenedioxy-2-aminoindane-N-L-tryptophanamide ("5,6-MDAI-tryptophanamide") and 3,4-methylenedioxyamphetamine-N-L-tryptophanamide ("3,4-MDA-tryptophanamide"), were tested in vitro for their solubility in aqueous solution and for their lipophilicity.

Aqueous solubility and lipophilicity can have important implications for pharmaceutical development. Firstly, both properties may affect the pharmacokinetics and bioavailability of the compounds in vivo. Secondly, these properties can help to determine the suitability of different compounds for development into different dosage forms.

Methods

Kinetic Turbidimetric Solubility Assay

Each test compound was diluted to 10 mM in dimethyl sulfoxide (DMSO). From this solution, six further dilutions of each test compound were prepared in DMSO (0.02, 0.1, 0.2, 1, 2, and 5 mM). Each of these solutions was then further diluted 1 in 50 in buffer (0.01 M phosphate buffered saline (pH 7.4)) so that the final DMSO concentration was 2% and the final test compound concentrations tested were 0.4, 2, 4, 20, 40, 100 and 200 μM. A DMSO blank was also included. Three replicate wells were designated per concentration. Following the dilutions in buffer, plates were incubated at room temperature shaking for 5 minutes before the absorbance was measured at 620 nM using a Molecular Devices SpectraMax384 UV detector. Nicardipine was tested as a control compound. 5,6-Methylenedioxy-2-aminoindane-N-L-tryptophanamide (5,6-MDAI-tryptophanamide) and 3,4-Methylenedioxyamphetamine-N-L-tryptophanamide (3,4-MDA-tryptophanamide) were prepared as hemioxalate salts.

Solubility was estimated from the concentration of test compound that produced an increase in absorbance above a threshold of 0.005 absorbance units and was normalised to the DMSO blank.

Micro Shake Flask Log D 10 mM solutions of each test compound were diluted in DMSO to give 400 μM solutions, which were then serially diluted into 2.5% DMSO in PBS to generate a calibration curve (0.014, 0.04, 0.12, 0.37, 1.11, 3.33 and 10 μM). 6 replicates of each test compound were incubated at 10 μM in a 1:9 ratio of Octanol:PBS at pH 7.4. Following a two hour incubation at room temperature shaking at 600 rpm, the incubation plate was centrifuged for 15 minutes to separate the layers and then two aliquots were removed from the PBS layer. The first was left neat and the second was diluted 10-fold to give dilute samples. Internal standards were added to both the calibration curve and the PBS incubation samples for analysis on LC MS/MS. Verapamil was tested as a control compound. 5,6-MDAI-tryptophanamide and 3,4-MDA-tryptophanamide were prepared as hemioxalate salts.

Log D was measured as the concentration in the PBS layer against the generated calibration curve relative to the starting concentration of 10 μM. All 6 replicates of the neat samples were averaged to give one value for each, with the same calculation performed for the dilute sample values.

Results

Kinetic Turbiditimetric Solubility Assay

TABLE 1

Maximum concentration of each compound tested in the solubility assay. The compounds were soluble at the concentrations shown.

| Compound ID | Maximum concentration tested | Solubility |
|---|---|---|
| Nicardipine | 200 μM | 24.4 μM |
| 5,6-MDAI-tryptophanamide | 200 μM | >200 μM |
| 3,4-MDA-tryptophanamide | 200 μM | >200 μM |

Micro Shake Flask Log D

TABLE 2

Mean LogD calculated for each compound using six replicates in the Micro shake flask assay.

| Compound ID | Mean LogD |
|---|---|
| Verapimil | 2.49 |
| 5,6-MDAI-tryptophanamide | 2.31 |
| 3,4-MDA-tryptophanamide | 1.97 |

Conclusions

Solubility:

Both novel compounds tested showed solubility up to 200 μM.

Lipophilicity:

Both novel compounds exhibited a Log D greater than 1.

The log D>1 seen for the novel compounds is consistent with a range reported to be optimal for orally-administered CNS drugs (Kerns EH and Di L (2008) Drug-like properties: concepts, structure design and methods: from ADME to toxicity optimization, ISBN 0123695201, Academic Press).

Example 13: Solubility and Lipophilicity of Novel Compounds

Introduction

Two novel compounds according to the invention, i.e. 3,4-methylenedioxyamphetamine-N-L-glycinamide ("3,4-MDA-glycinamide") and 3,4-methylenedioxymethamphetamine-N-L-glycinamide ("3,4-MDMA-glycinamide"), were tested in vitro for their solubility in aqueous solution and for their lipophilicity, as compared to MDMA.

Methods

Kinetic Turbidimetric Solubility Assay

Each test compound was diluted to 10 mM in dimethyl sulfoxide (DMSO). From this solution, six further dilutions of each test compound were prepared in DMSO (0.02, 0.1, 0.2, 1, 2, and 5 mM). Each of these solutions was then further diluted 1 in 50 in buffer (0.01 M phosphate buffered saline (pH7.4)) so that the final DMSO concentration was 2% and the final test compound concentrations tested were 0.4, 2, 4, 20, 40, 100 and 200 μM. A DMSO blank was also included. Three replicate wells were designated per concentration. Following the dilutions in buffer, plates were incubated at room temperature shaking for 5 minutes before the absorbance was measured at 620 nM using a Molecular Devices SpectraMax384 UV detector. Nicardipine was tested as a control compound. 3,4-Methylenedioxyamphetamine-N-L-glycinamide (3,4-MDA-glycinamide) and 3,4-Methylenedioxymethamphetamine-N-L-glycinamide (3,4-MDMA-glycinamide) were prepared as hemioxalate salts.

Solubility was estimated from the concentration of test compound that produced an increase in absorbance above a threshold of 0.005 absorbance units and was normalised to the DMSO blank.

Micro Shake Flask Log D 10 mM solutions of each test compound were diluted in DMSO to give 400 μM solutions, which were then serially diluted into 2.5% DMSO in PBS to generate a calibration curve (0.014, 0.04, 0.12, 0.37, 1.11, 3.33 and 10 μM). 6 replicates of each test compound were incubated at 10 μM in a 1:9 ratio of Octanol:PBS at pH 7.4. Following a two hour incubation at room temperature shaking at 600 rpm, the incubation plate was centrifuged for 15 minutes to separate the layers and then two aliquots were removed from the PBS layer. The first was left neat and the second was diluted 10-fold to give dilute samples. Internal standards were added to both the calibration curve and the PBS incubation samples for analysis on LC MS/MS. Verapamil was tested as a control compound. 3,4-MDA-glycinamide and 3,4-MDMA-glycinamide were prepared as hemioxalate salts.

Log D was measured as the concentration in the PBS layer against the generated calibration curve relative to the starting concentration of 10 μM. All 6 replicates of the neat samples were averaged to give one value for each, with the same calculation performed for the dilute sample values.

Results

Kinetic Turbiditimetric Solubility Assay

TABLE 3

Maximum concentration of each compound tested in the solubility assay. The compounds were soluble at the concentrations shown.

| Compound ID | Maximum concentration tested | Solubility |
|---|---|---|
| Nicardipine | 200 μM | 22.1 μM |
| MDMA | 200 μM | >200 μM |
| 3,4-MDA-glycinamide | 200 μM | >200 μM |
| 3,4-MDMA-glycinamide | 200 μM | >200 μM |

Micro Shake Flask Log D

TABLE 4

Mean LogD calculated for each compound using six replicates in the Micro shake flask assay.

| Compound ID | Mean LogD |
|---|---|
| Verapimil | 2.30 |
| MDMA | 0.57 |
| 3,4-MDA-glycinamide | 1.08 |
| 3,4-MDMA-glycinamide | 0.66 |

Conclusions

Solubility:

MDMA, 3,4-MDA-glycinamide, and 3,4-MDMA-glycinamide showed solubility up to 200 μM.

Lipophilicity:

The Log D for 3,4-MDMA-glycinamide was similar to that of MDMA.

The Log D for 3,4-MDA-glycinamide was slightly greater than that of MDMA.

The log D>1 seen for the novel compounds is consistent with a range reported to be optimal for orally-administered CNS drugs (Kerns EH and Di L (2008) Drug-like properties: concepts, structure design and methods: from ADME to toxicity optimization, ISBN 0123695201, Academic Press).

Example 14: Locomotor Activity and Neurotransmitter Release in Rats Following Oral Dosing with Novel Compounds Introduction Two novel test compounds according to the invention, i.e. 5,6-methylenedioxy-2-aminoindane-N-L-tryptophanamide ("5,6-MDAI-tryptophanamide") and 3,4-methylenedioxyamphetamine-N-L-tryptophanamide ("3,4-MDA-tryptophanamide"), were assessed for their effects on locomotor activity and monoamine neurotransmitter release in the rat, as compared to MDMA.

MDMA was selected as a comparator due to the extensive supporting literature and its current progress in clinical development as a potential treatment for mental health disorders. MDMA has previously been shown to induce hyperlocomotion and behavioural measures of serotonin syndrome in rats, as well as elevations in monoamine neurotransmitter levels (Baumann M H et al. (2008) *Pharmacol. Biochem. Behay.* 90, 208-217. doi:10.1016/j.pbb.2008.02.018).

Methods

Experimental Animals

Male Sprague Dawley rats weighing 250-350 g at time of purchase (Charles River UK) were group housed in cages on a normal phase 12 hr light-dark cycle (lights on from 07:00-19:00) with ad libitum access to standard pelleted diet and filtered tap water. The holding room was maintained at 21±4° C. with a relative humidity of 55±15%.

Experimental Procedures

Surgery

Single-probe dialysis was performed, whereby a probe (CMA 12 Eite; 2 mm membrane tip) was stereotaxically implanted into the nucleus accumbens (AP+2.2 mm, ML±1.5 MM, DV-8 mm, relative to skull surface) of each rat. The upper incisor bar was set at 3.3 mm below the interaural line so that the skull surface between bregma and lamba was horizontal. Additional burr holes were made for the skull screws (stainless steel) and probes were secured using dental cement. The scalp was sutured and the wound dressed with an antiseptic spray and plastic dressing. Rats were administered carprofen (5 mg/kg, subcutaneous) for pain relief at least 30 mins prior to regaining consciousness. The rats were allowed a recovery period of at least 16 hours with food and water available ad libitum, during which time the probes were contiuously perfused with an artificial cerebrospinal fluid (aCSF, Harvard Apparatus, UK) at a flow rate of 1.2 μl/min. Rats were placed in dialysis bowls with their microdialysis probes connected to a swivel and a counter-balanced arm to allow unrestricted movement, ready for the microdialysis experiment.

Microdialysis

The day after surgery, dialysate samples were collected at 20 minute intervals from 80 minutes prior to 2 hour following oral administration of vehicle (0.9% saline), MDMA, 5,6-Methylenedioxy-2-aminoindane-N-L-tryptophanamide (5,6-MDAI-tryptophanamide) hemioxalate or 3,4-Methylenedioxyamphetamine-N-L-tryptophanamide (3,4-MDA-tryptophanamide) hemioxalate. Test compounds were prepared in vehicle solution and administered orally using a dose volume of 10 ml/kg. Doses given for compounds in salt form were adjusted to ensure equivalent dose of drug (5 mg/kg) across all treatment groups.

The dosing groups used are summarised in Table 5 below:

TABLE 5

| Test compound | Route | Dose | n |
|---|---|---|---|
| Vehicle | PO | — | 8 |
| MDMA | PO | 5 mg/kg | 8 |
| 5,6-MDAI-tryptophanamide | PO | 5 mg/kg | 8 |
| 3,4-MDA-tryptophanamide | PO | 5 mg/kg | 8 |

Dialysates were collected into vials containing 0.1 M perchloric acid to prevent oxidation of the neurotransmitters. Dialysate samples were subsequently assayed by HPLC.

HPLC Analysis

Samples were analysed for dopamine (DA), noradrenaline (NA) and serotonin (5-HT) by HPLC based on reverse-phase, ion-pair HPLC coupled with electrochemical detection and the use of an ALEXYS® monoamine analyser (Antec Leyden, The Netherlands). The system consists of two separate analytical columns (Intersil™ 3 μm) that share a dual-loop autosampler allowing one sample to be simultaneously analysed by two systems optimised for different neurotransmitters, with one column measuring DA and 5-HT and the other analysing NA. Two solvent delivery pumps (LC 110) circulate the respective mobile phases at a flow rate of 50 μl/min and an Antec in-line degassing unit removes air. Samples are injected onto the columns via an autosampler (AS 110) with a cooling tray set at 4° C. Antec DECADE II® electrochemical detectors are used and Antec micro VT 03 cells employing high-density, glassy carbon working electrodes combined with an Ag/AgCl reference electrodes. The electrode signals were integrated using Antec's CLARITY® data acquisition system. The sensitivity of the system was verified prior to onset of sample analysis by performing a standard concentration curve (e.g. 4 concentrations) spanning either side of the expected basal value of the transmitter.

Locomotor Activity and Behavioural Observations

Locomotor activity was tracked continuously from 60 minutes prior to treatment, up to 2 hours post-treatment using EthoVision XT video tracking software. Animals were tracked using center-point detection. The EthoVision software was then used to analyse the videos and generate data for various locomotor activity parameters.

Rats were also observed for behavioural measures of serotonin syndrome (e.g. rearing, forepaw treading) for a 30 second period, 1 minute into every 20 minute sampling period post-treatment. Behaviours were also observed, but not scored, in the 30 seconds prior to treatment to acclimatise the rats to the assessor's presence. The behaviours observed post-treatment were scored blindly by an independent assessor depending on the proportion of the 30 second period in which the behaviour was observed: 0=absent (0%), 1—mild (~0-30%), 2=moderate (~30-70%), 3=intense (~70-100%).

Data Analysis

Microdialysis data were log transformed. Baseline was defined as the geometric mean of the four pre-treatment samples (i.e. those collected at −60 min, −40 min, −20 min and 0 min). Analysis was by analysis of covariance with log(baseline) as a covariate. All data (except samples with poor chromatography) were included in the analysis. Each time was analysed separately, together with means during each of the two hours after dosing and the overall 0-2 hours after dosing. For calculation of hourly and overall means, missing data were imputed to be the geometric mean of the previous and subsequent values (if the 100-120 minute value was missing, it was imputed to be equal to the 80-100 minute value).

Ethovision data were square root transformed. Baseline was defined as the mean of the four pre-treatment samples (i.e. those collected at −60 min, −40 min, −20 min and 0 min). Analysis was by analysis of covariance with sqrt (baseline) as a covariate.

Comparisons to vehicle were by the multiple t test.

Behaviour data were analysed for each behaviour and at each time separately by exact Wilcoxon Rank Sum tests to compare each treatment to vehicle.

Results

Figure 9:
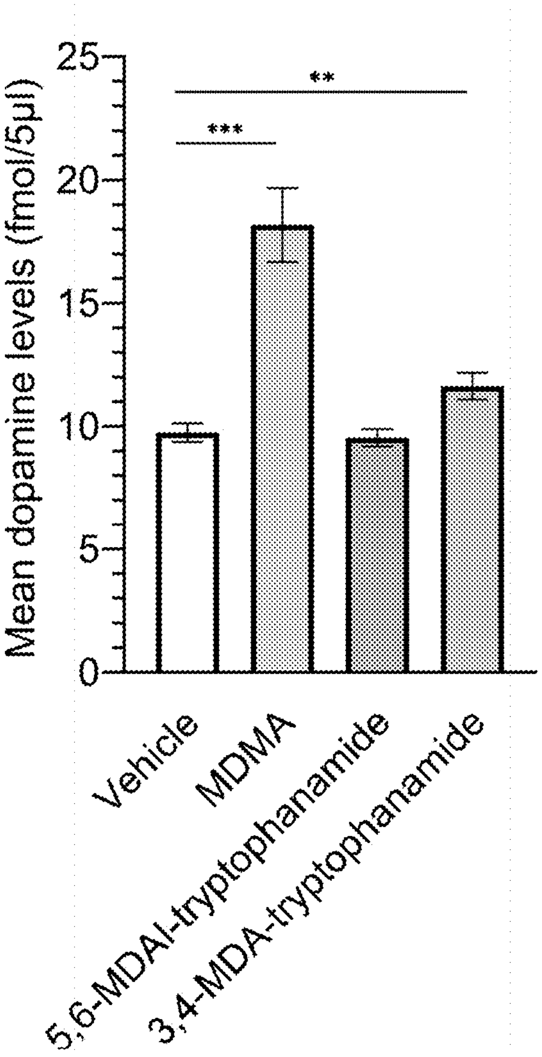
FIG. 9: Mean dopamine levels measured in nucleus accumbens over 2 hour period following oral dosing of rats with test compounds. Data shown as mean±SEM. Statistical significance calculated compared to vehicle:  $p<0.01$; * $p<0.001$. See Example 14.
Figure 10:
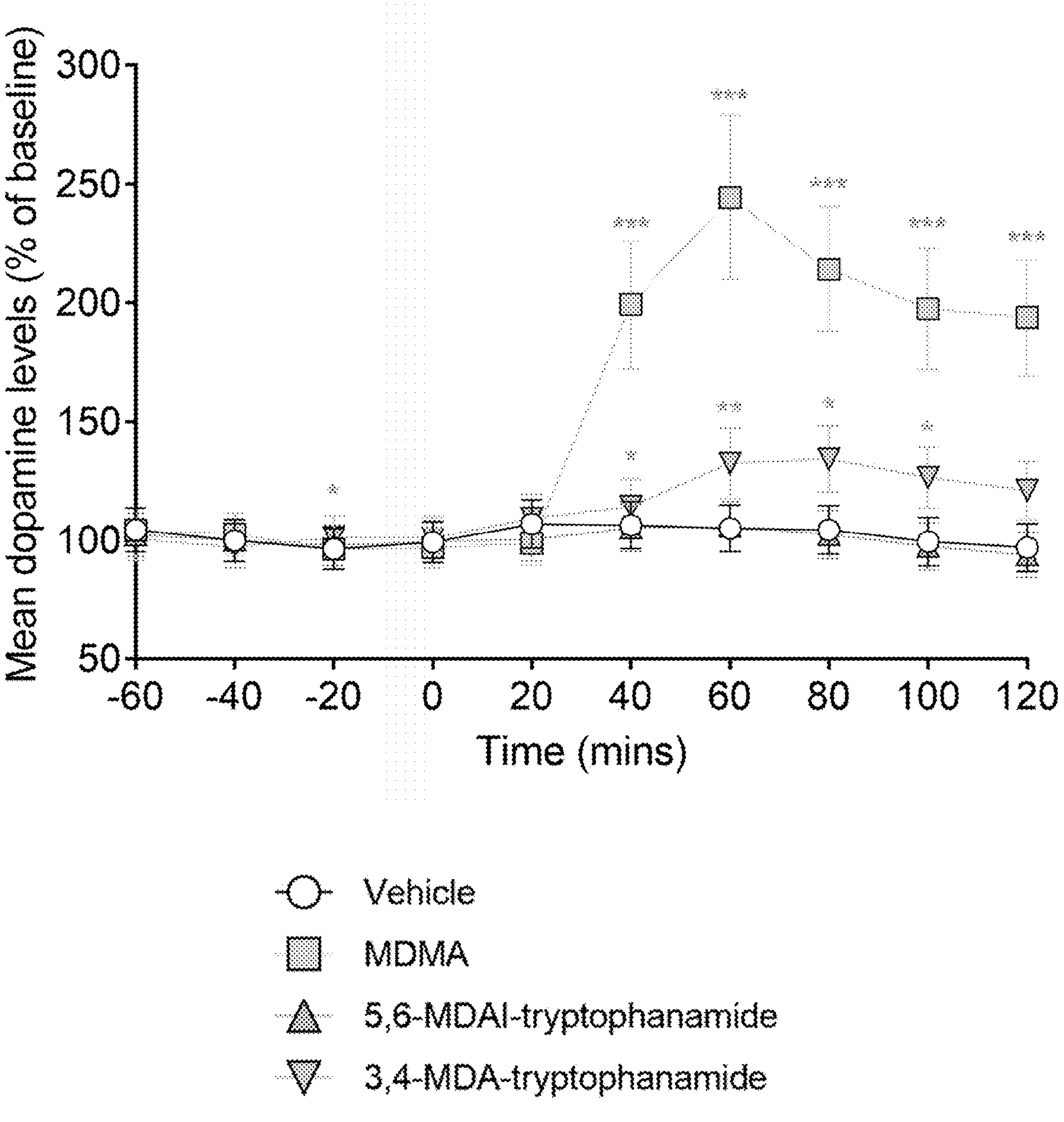
FIG. 10: Mean dopamine levels (% of baseline) measured in nucleus accumbens prior to and following oral dosing of rats with test compounds (dosing occurred at 0 minutes). Data shown as mean±SEM. Statistical significance shown as compared to vehicle: * $p<0.05$;  $p<0.01$; * $p<0.001$. See Example 14.
Figure 11:
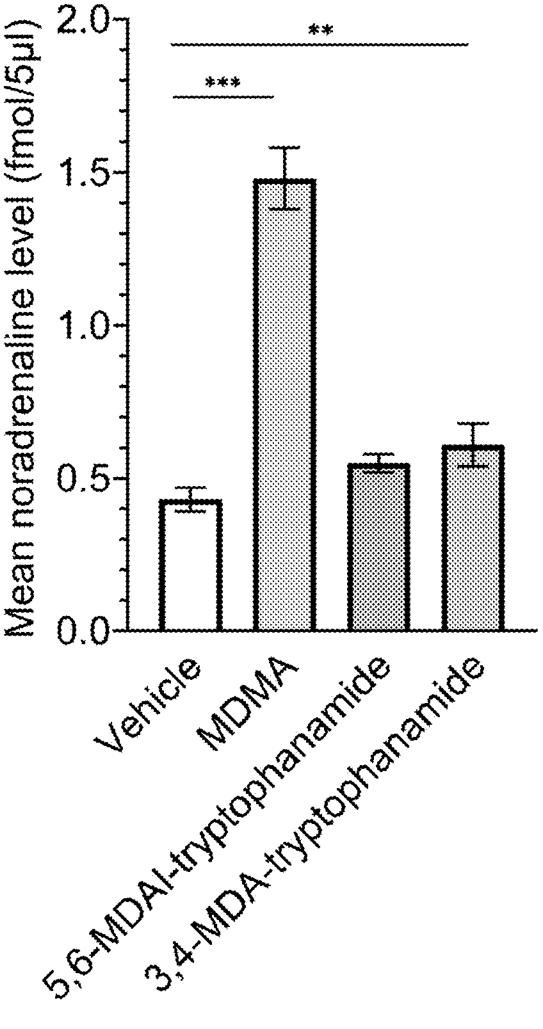
FIG. 11: Mean noradrenaline levels measured in nucleus accumbens over 2 hour period following oral dosing of rats with test compounds. Data shown as mean±SEM. Statistical significance calculated compared to vehicle:  $p<0.01$; * $p<0.001$. See Example 14.
Figure 12:
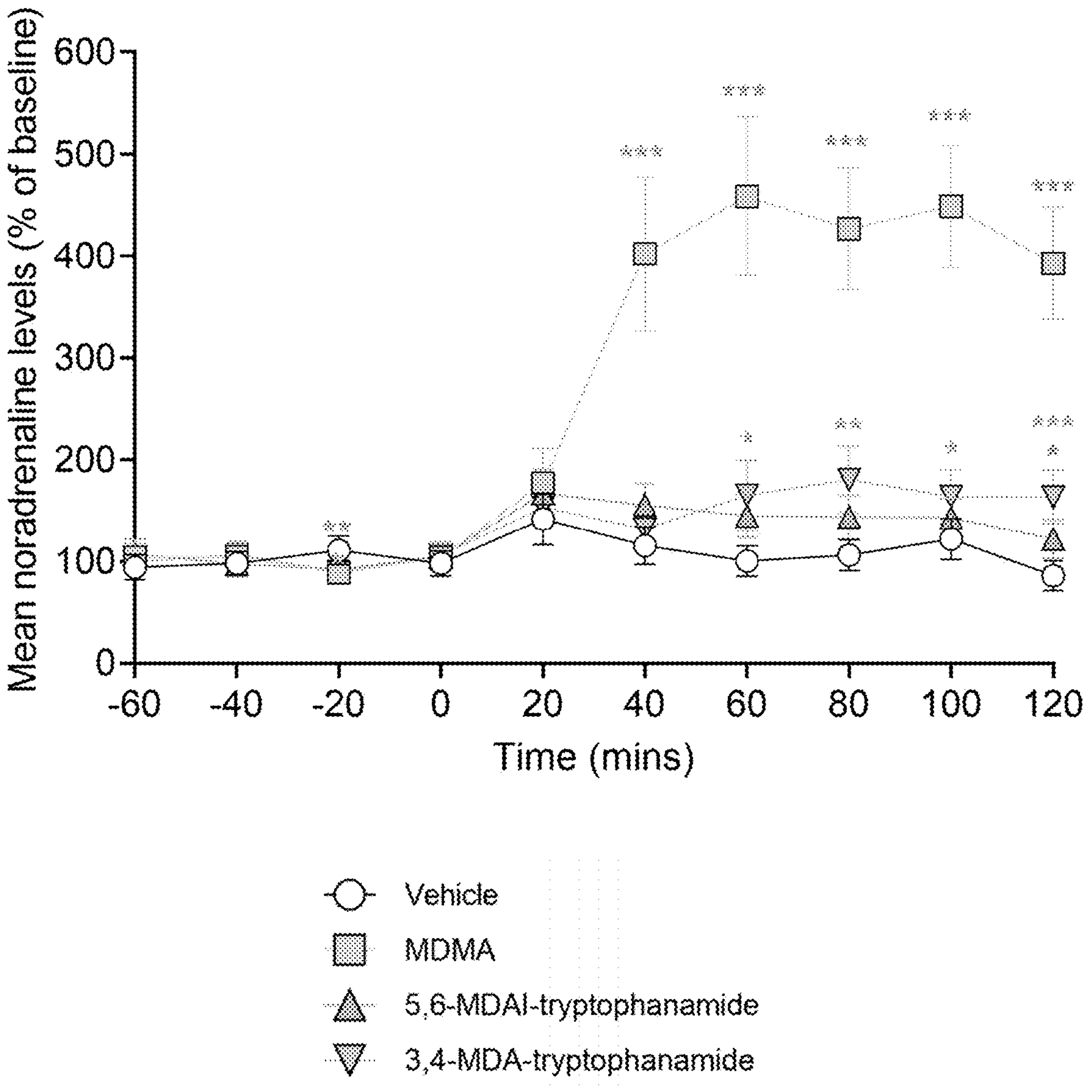
FIG. 12: Mean noradrenaline levels (% of baseline) measured in nucleus accumbens prior to and following oral dosing of rats with test compounds (dosing occurred at 0 minutes). Data shown as mean±SEM. Statistical significance shown as compared to vehicle: * $p<0.05$;  $p<0.01$; * $p<0.001$. See Example 14.
Figure 13:
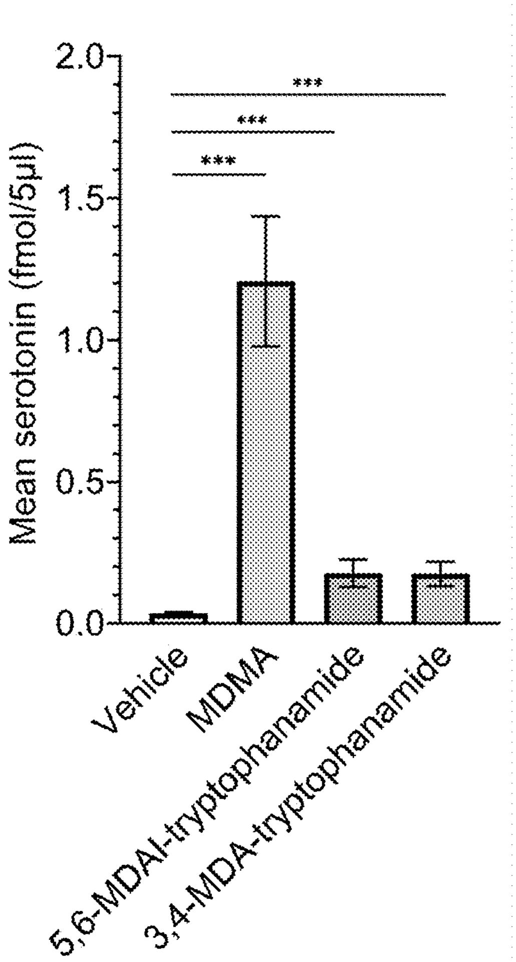
FIG. 13: Mean serotonin levels measured in nucleus accumbens over 2 hour period following oral dosing of rats with test compounds. Data shown as mean±SEM. Statistical significance calculated compared to vehicle: *** $p<0.001$. See Example 14.
Figure 14:
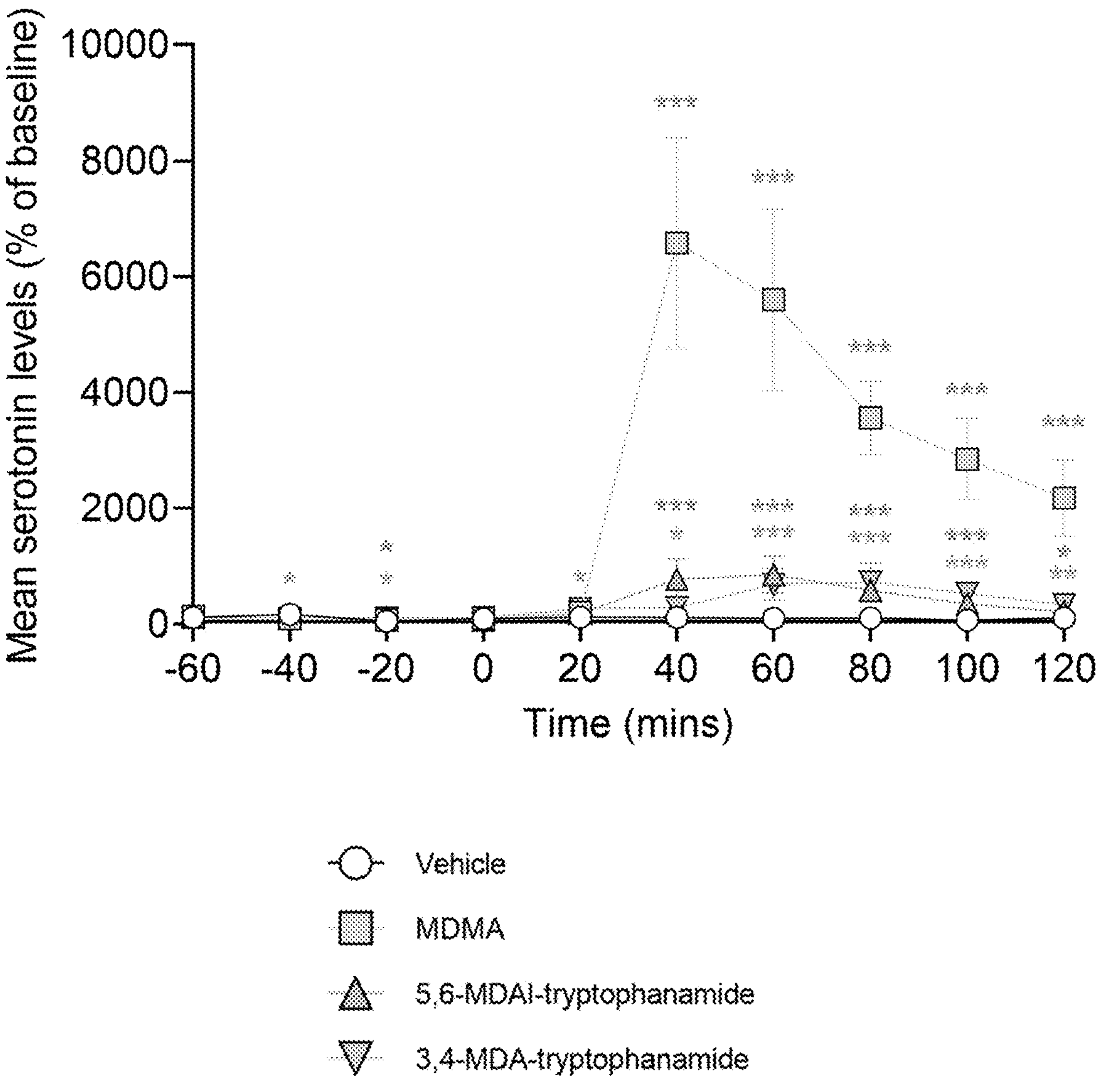
FIG. 14: Mean serotonin levels (% of baseline) measured in nucleus accumbens prior to and following oral dosing of rats with test compounds (dosing occurred at 0 minutes). Data shown as mean±SEM. Statistical significance shown as compared to vehicle: * $p<0.05$;  $p<0.01$; * $p<0.001$. See Example 14.

The results obtained are shown in the following Tables 6 and 7 as well as in FIGS. 9 to 14.

TABLE 6

Summary of effects of each treatment on locomotor activity. Effects shown are significant changes in total distance travelled as compared to the vehicle group.

| Test compound | Effect on locomotor activity | | |
|---|---|---|---|
| | 0-60 mins | 60-120 mins | 0-120 mins |
| Vehicle | — | — | — |
| MDMA | ↑↑↑ | ↑↑↑ | ↑↑↑ |
| 5,6-MDAI-tryptophanamide | — | — | — |
| 3,4-MDA-tryptophanamide | — | — | — |

Note:
↑↑↑, $p < 0.001$.

TABLE 7

Summary of behavioural observations scored post-treatment. Observations shown were significantly increased as compared to the vehicle group. No significant increases were identified for other behaviours assessed, including head weaving or forepaw treading.

| Test compound | Observations (approximate timecourse) |
|---|---|
| Vehicle | None |
| MDMA | Flattened posture (~0-40 mins) and hind limb abduction (~0-40 mins) |
| 5,6-MDAI-tryptophanamide | None |
| 3,4-MDA-tryptophanamide | None |

Conclusions

Both 5,6-MDAI-tryptophanamide and 3,4-MDA-tryptophanamide caused significant increases in serotonin levels in nucleus accumbens, as compared to the vehicle group. The effects were smaller in magnitude compared to MDMA.

3,4-MDA-tryptophanamide also caused significant increases in dopamine and noradrenaline levels in nucleus accumbens, as compared to the vehicle group. The effects were smaller in magnitude compared to MDMA.

The invention claimed is:

1. A compound according to the general formula (I):

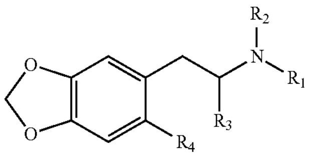

(I)

wherein:

$R_1$ is selected from

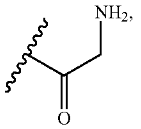
,
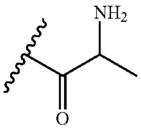
,
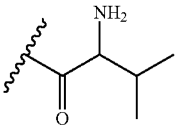
,
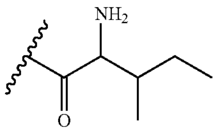
,
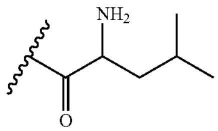
,

-continued

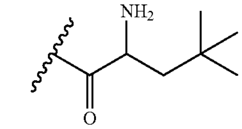
,
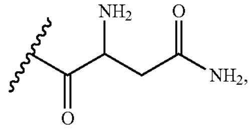

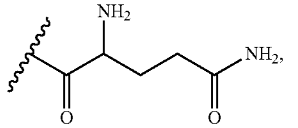
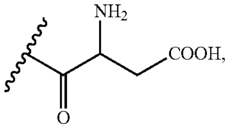

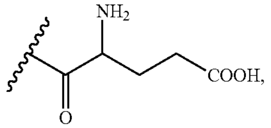

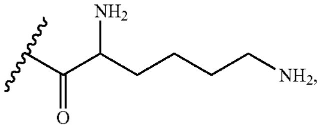
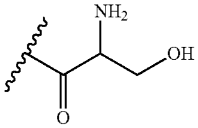
,

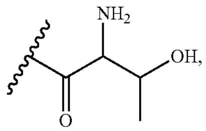
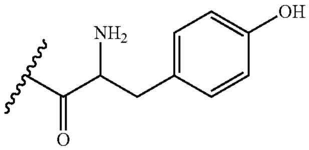
,

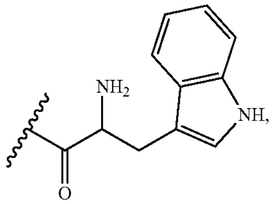
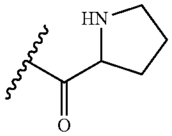
,

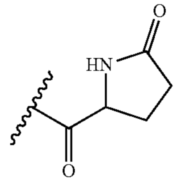
, and
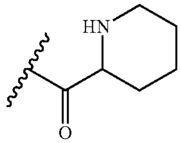
;

$R_2$ is —H or —$CH_3$; and $R_3$ is —$CH_3$, and $R_4$ is —H or —$OCH_3$, or $R_3$ and $R_4$ are mutually joined to form a group —$CH_2$—;

or a pharmaceutically acceptable salt thereof;

with the proviso that if $R_2$ is —H, $R_3$ is —$CH_3$ and $R_4$ is —H, then $R_1$ is not

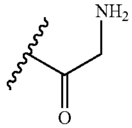
,
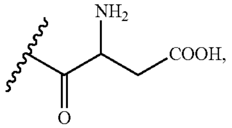
or
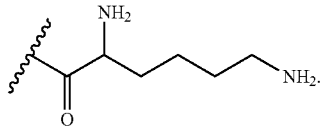

2. The compound of claim 1, wherein $R_2$ is —H, $R_3$ is —$CH_3$, and $R_4$ is —H.

3. The compound of claim 1, wherein $R_2$ is —$CH_3$, $R_3$ is —$CH_3$, and $R_4$ is —H.

4. The compound of claim 1, wherein $R_2$ is —H, $R_3$ is —$CH_3$, and $R_4$ is —$OCH_3$.

5. The compound of claim 1, wherein $R_2$ is —H, and wherein $R_3$ and $R_4$ are mutually joined to form a group —$CH_2$—.

6. The compound of claim 1, wherein $R_1$ is selected from:

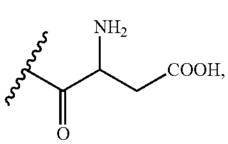
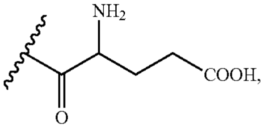

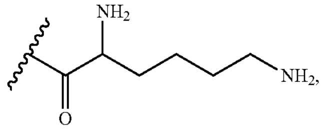

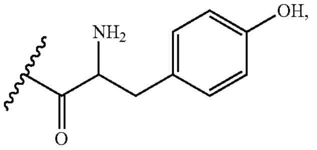
and

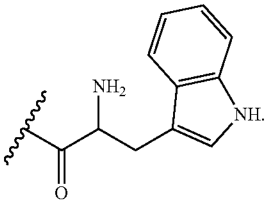

7. The compound of claim 1, wherein $R_1$ is

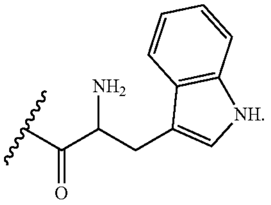

8. The compound of claim 1, wherein said compound is selected from any one of the following compounds:

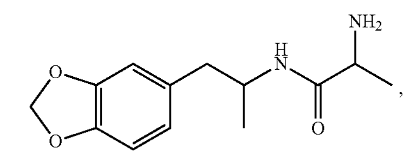
,

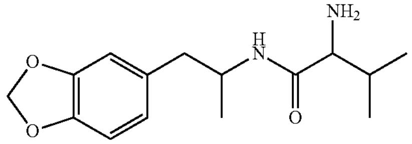
,

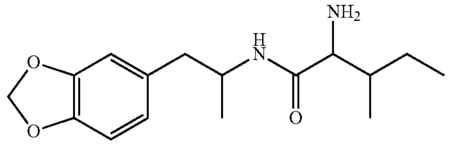
,

-continued
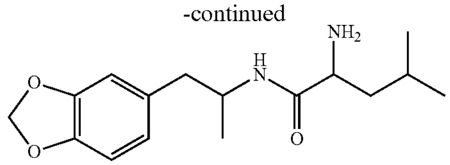
,
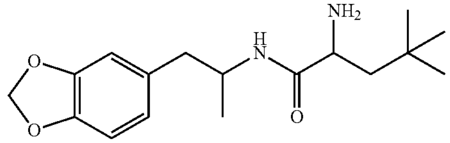
,
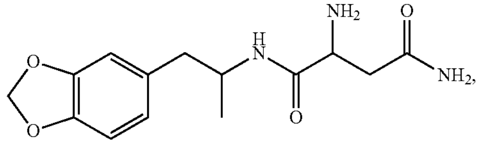
,
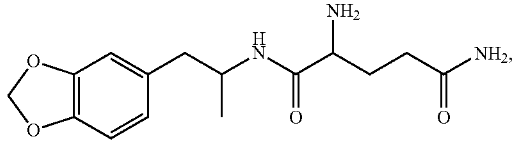
,
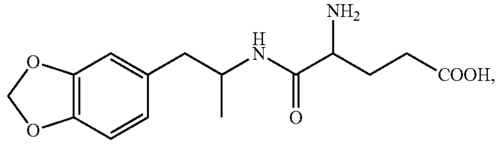
,
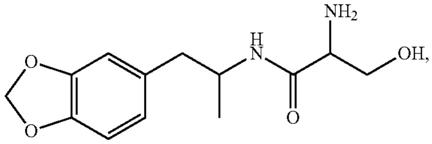
,
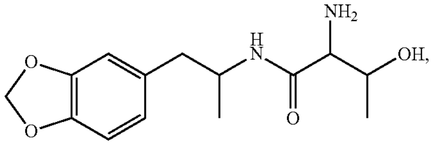
,
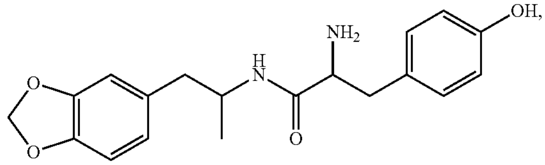
,
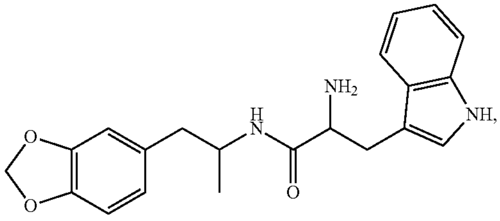
,
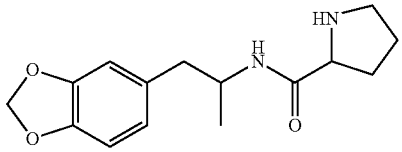
,
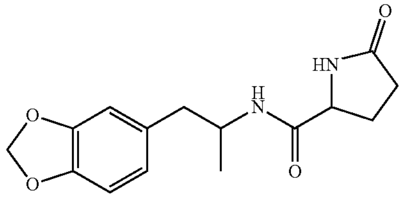
,
-continued
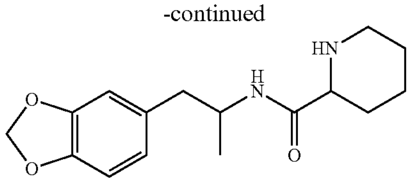
,
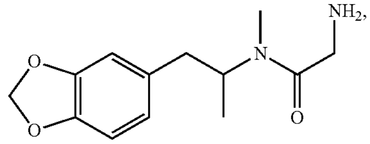
,
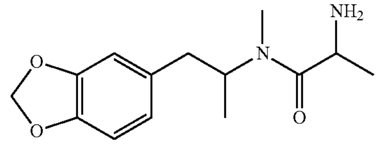
,
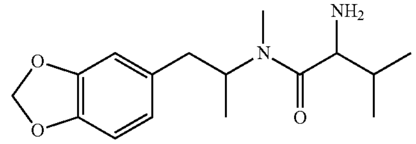
,
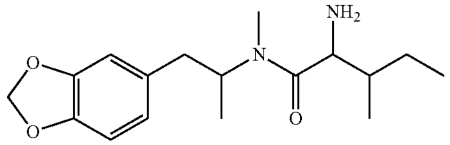
,
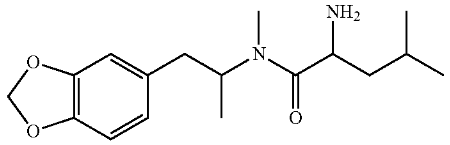
,
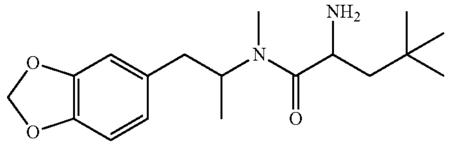
,
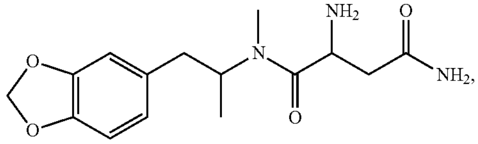
,
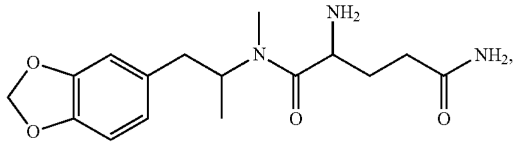
,
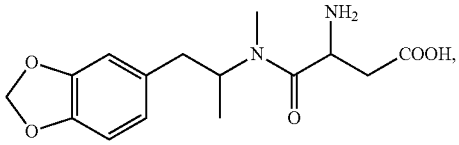
,
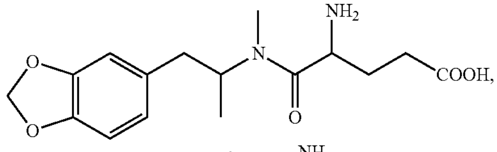
,
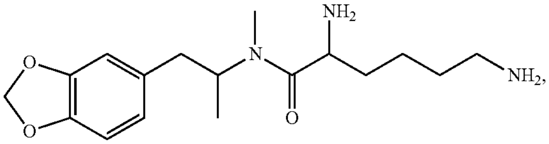
, -continued
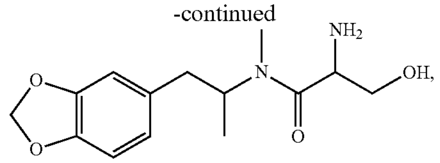,
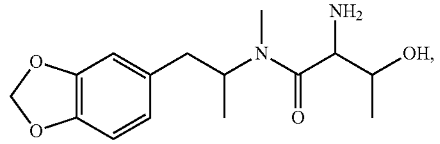,
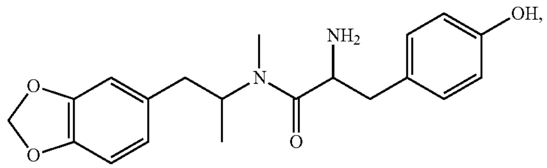,
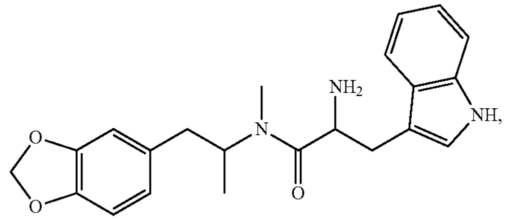,
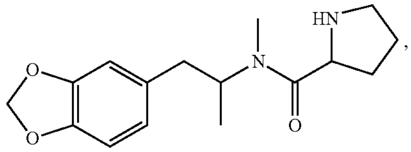,
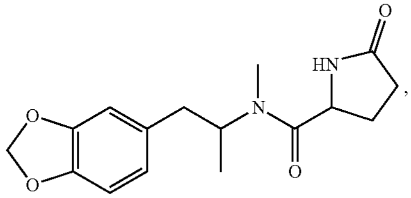,
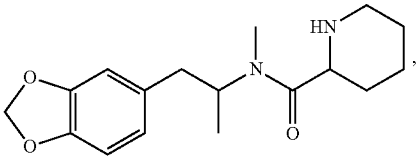,
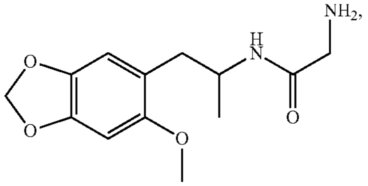,
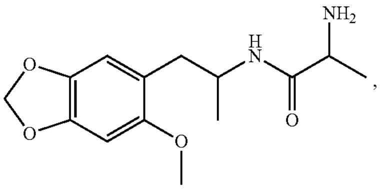,
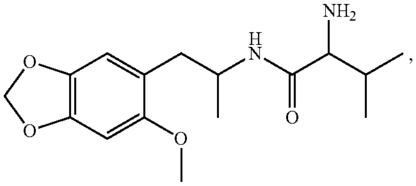,
-continued
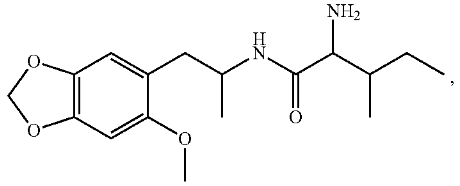,
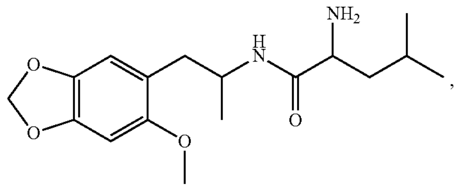,
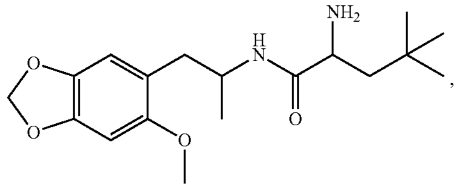,
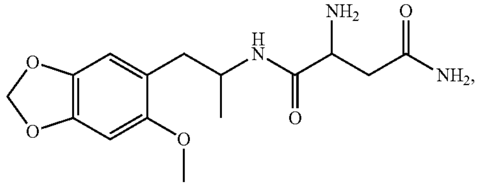,
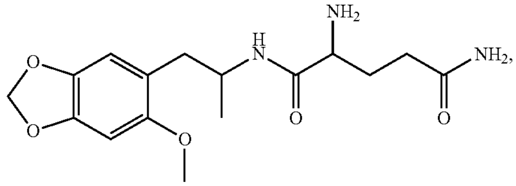,
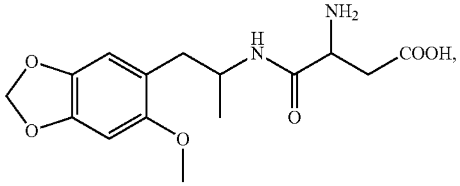,
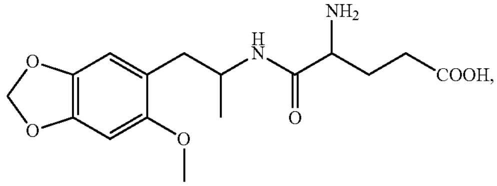,
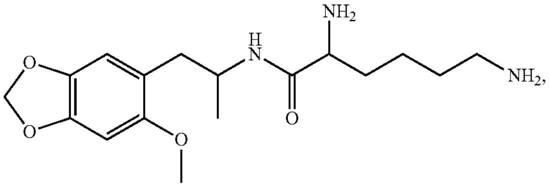,
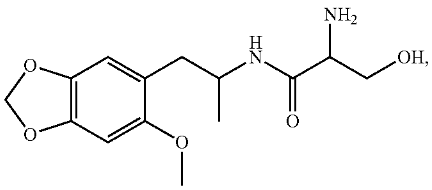, -continued
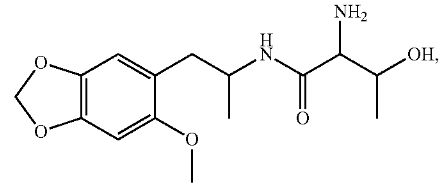
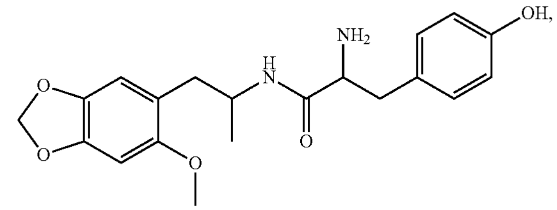
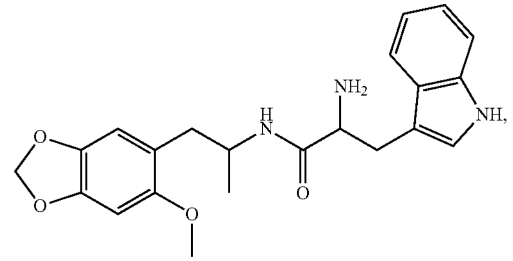
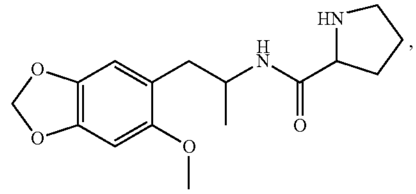
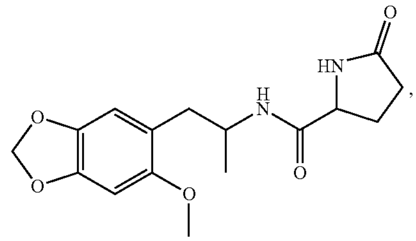
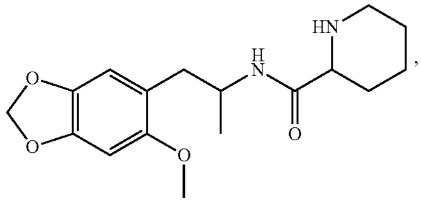
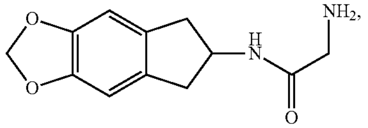
-continued
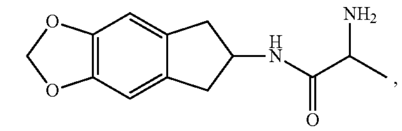
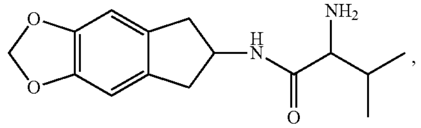
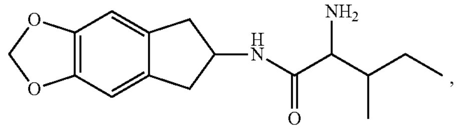
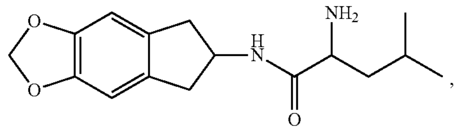
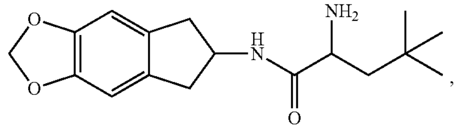
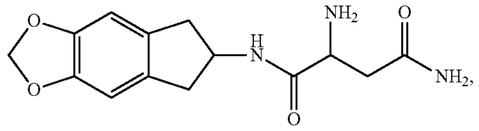
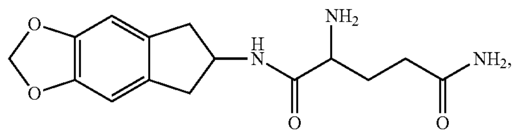
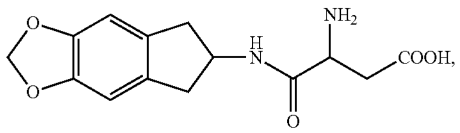
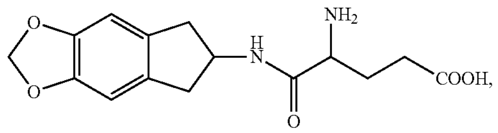

-continued

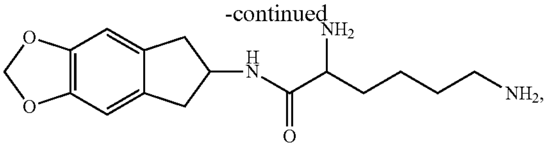

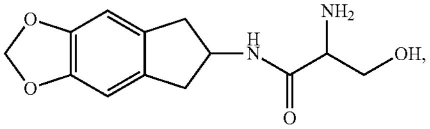

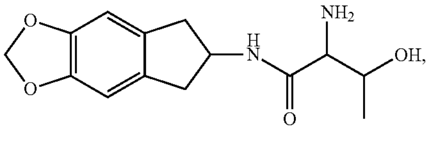

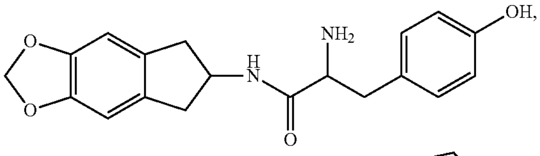

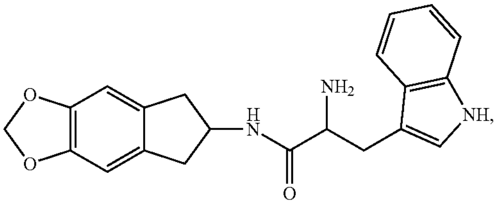

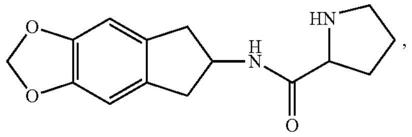

-continued

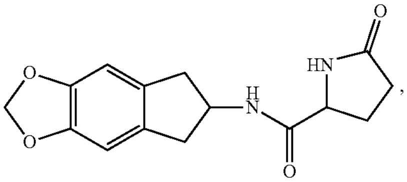

or

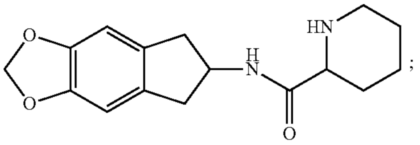

or a pharmaceutically acceptable salt thereof.

9. A pharmaceutical composition comprising at least one compound of claim 1 and one or more pharmaceutically acceptable excipients.

10. A method of treating a serotonin 5-$HT_{2A}$ receptor associated disease/disorder in a subject in need thereof, the method comprising administering a therapeutically effective amount of the compound of claim 1 to said subject.

11. The method of claim 10, wherein said disease/disorder is an anxiety disorder, attention deficit hyperactivity disorder (ADHD), posttraumatic stress disorder (PTSD), depression, cluster headache, a condition associated with cancer, diminished drive, burn-out, bore-out, migraine, Parkinson's disease, pulmonary hypertension, schizophrenia, an eating disorder, nausea, or vomiting.

12. A method for the production of a compound according to claim 1, comprising the steps of:

- a. preparing a solution of a protected amino acid in solvent I;
- b. addition of an activating agent dissolved in solvent I under protective gas atmosphere;
- c. stirring of the mixture under protective gas atmosphere for at least 2 hours at room temperature;
- d. safrylamine (as a free base) dissolved in solvent I is added dropwise under protective gas atmosphere;
- e. stirring of the mixture under protective gas atmosphere for at least 2 hours at room temperature;
- f. stopping the reaction by adding 2% ammonia solution;
- g1. concentration of the solvent I;
- g2. dissolving the residue in solvent II;
- h. extraction with 1M HCl, water and saturated saline solution;
- i. drying of the organic phase over a desiccant at 40-60° C. and under vacuum;
- j. obtaining the crude product;
- k. purification of the crude product by recrystallization and/or column chromatography;
- l. obtaining the protected safrylamine peptide;
- m. deprotection of the protected safrylamine peptide;
- n. purification of the safrylamine peptide by means of column chromatography;
- o. obtaining the safrylamine peptide.

13. The method of production according to claim 12, wherein:

(i) the safrylamine is selected from the group consisting of 3,4-methylenedioxy-N-methylamphetamine (MDMA), 3,4-methylenedioxyamphetamine (MDA), 2-methoxy-4,5-methylenedioxyamphetamine (MMDA-2), and 5,6-methylenedioxy-2-aminoindane (MDAI); and/or (ii) the activating agent is selected from the group consisting of 1,1'-carbonyldiimidazole, triethylamine, diisopropylethylamine, pyridine and 4-dimethylaminopyridine, dicyclohexylcarbodiimide (DCC), diisopropylcarbodiimide (DIC), 1-ethyl-3-(3-dimethylaminopropyl) carbodiimide (EDC), 1-[bis(dimethylamino) methylene]-1H-1,2,3-triazolo[4,5-b]pyridinium 3-oxide hexafluorophosphate (HATU), and (benzotriazol-1-yloxy)tripyrrolidinophosphonium hexafluorophosphate (PyBOP), or a combination thereof; and/or (iii) the protected amino acid is selected from the group consisting of N-(9-fluorenylmethyloxycarbonyl)-L-tryptophan, N,N'-di-carbobenzoxy-L-lysine, 1-benzyl-N-carbobenzoxy-L-glutamate, N-carbobenzoxy-L-tyrosine, and 4-benzyl N-carbobenzoxy-L-aspartate; and/or (iv) the solvent I is selected from the group consisting of tetrahydrofuran, 2-methyltetrahydrofuran, and dioxane; and/or (v) the solvent II is selected from the group consisting of diethylether, methyl-tert-butylether, chloroform, and dichloromethane, or a combination thereof; and/or (vi) the yield of the safrylamine peptide is at least 45 wt.-% relative to the starting materials.

* * * * *